(12) United States Patent
Owens et al.

(10) Patent No.: US 7,858,756 B2
(45) Date of Patent: Dec. 28, 2010

(54) MONOCLONAL ANTIBODIES THAT SELECTIVELY RECOGNIZE METHAMPHETAMINE AND METHAMPHETAMINE LIKE COMPOUNDS

(75) Inventors: S. Michael Owens, Little Rock, AR (US); Melinda Gunnell, Conway, AR (US); Yingni Chi, Little Rock, AR (US); F. Ivy Carroll, Durham, NC (US); Ralph Henry, Fayetteville, AR (US); Eric Peterson, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 490 days.

(21) Appl. No.: 11/763,948

(22) Filed: Jun. 15, 2007

(65) Prior Publication Data

US 2008/0125579 A1 May 29, 2008

Related U.S. Application Data

(60) Provisional application No. 60/913,124, filed on Apr. 20, 2007, provisional application No. 60/813,917, filed on Jun. 15, 2006.

(51) Int. Cl.
*C07K 16/00* (2006.01)
*A61K 39/395* (2006.01)
*G01N 33/53* (2006.01)

(52) U.S. Cl. .................. 530/388.1; 424/130.1; 435/7.1

(58) Field of Classification Search ............. 530/387.1, 530/388.1; 424/130.1; 435/7.1
See application file for complete search history.

(56) References Cited

U.S. PATENT DOCUMENTS

| | | | |
|---|---|---|---|
| 4,041,076 A | 8/1977 | Avenia et al. | |
| 4,329,281 A | 5/1982 | Christenson et al. | |
| 4,816,567 A | 3/1989 | Cabilly et al. | |
| 5,041,076 A | 8/1991 | Kantor | |
| 5,135,863 A | 8/1992 | Hu et al. | |
| 5,141,850 A | 8/1992 | Cole et al. | |
| 5,160,701 A | 11/1992 | Brown, III et al. | |
| 5,238,652 A | 8/1993 | Sun et al. | |
| 5,328,828 A | 7/1994 | Hu et al. | |
| 5,415,994 A | 5/1995 | Imrich et al. | |
| 5,451,504 A | 9/1995 | Fitzpatrick et al. | |
| 5,492,841 A | 2/1996 | Craig | |
| 5,545,806 A | 8/1996 | Lonberg et al. | |
| 5,545,807 A | 8/1996 | Surani et al. | |
| 5,559,041 A | 9/1996 | Kang et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,976,812 A | 11/1999 | Huber et al. | |
| 6,087,184 A | 7/2000 | Magginetti et al. | |
| 6,306,616 B1 | 10/2001 | Shindelman | |
| 6,669,937 B2 | 12/2003 | Owens et al. | |
| 7,037,669 B2 | 5/2006 | Zheng et al. | |
| 7,202,348 B2 | 4/2007 | Owens et al. | |
| 2003/0119083 A1 | 6/2003 | Owens et al. | |
| 2003/0171435 A1 | 9/2003 | Pouletty et al. | |

FOREIGN PATENT DOCUMENTS

| | | |
|---|---|---|
| EP | 0239400 A2 | 9/1987 |
| EP | 0343346 A1 | 11/1989 |
| EP | 0574782 A2 | 12/1993 |
| EP | 0375422 B1 | 7/1996 |
| EP | 1331219 A1 | 7/2003 |
| WO | 86/01533 A1 | 3/1986 |
| WO | 92/03163 A1 | 5/1992 |
| WO | 97/49732 A1 | 12/1997 |
| WO | 01/81424 A1 | 11/2001 |
| WO | 2004/050032 A2 | 7/2004 |
| WO | 2007/147122 A2 | 12/2007 |

OTHER PUBLICATIONS

International Search Report for PCT/US07/71354 dated Mar. 10, 2008, 10 pages.
Cho, et al., Relevance of Pharmacokinetic Parameters in Animal Models of Methamphetamine Abuse, 2001, pp. 161-166, Synapse, vol. 39.
Sato, et al., Relapse of Paranoid Psychotic State in Methamphetamine Model of Schizophrenia, 1992, pp. 115-122, Schizophrenia Bulletin, vol. 18, No. 1.
Valentine, et al., Antiphencyclidine Monoclonal Antibody Therapy Significantly Changes Phencyclidine Concentrations in Brain and Other Tissues in Rats, 1996, pp. 717-724, JPET, vol. 278, No. 2.
Valentine, et al., Antiphencyclidine Monoclonal Fab Fragments Reverse Phencyclidine-Induced Behavioral Effects and Ataxia in Rats, 1996, pp. 709-716, JPET, vol. 278, No. 2.
International Search Report dated Oct. 10, 2001.
Albertson et al, "Methamphetamine and the Expanding Complications of Amphetamines", West J. Med, 1999, pp. 214-219 vol. 170, No. 4.
Aoki et al, "Immunoassay For Methamphetamine With A New Antibody", Forensic Science International, 1990, pp. 245-255, vol. 44.
Byrnes-Blake et al, "Generation of anti-(+)methamphetamine antibodies is not impeded by (+) methamphetamine administration during active immunization of rats", International Immunopharmacology, 2001, pp. 329-338, vol. 1.

(Continued)

*Primary Examiner*—Larry R Helms
*Assistant Examiner*—Hong Sang
(74) *Attorney, Agent, or Firm*—Polsinelli Shughart PC

(57) ABSTRACT

The invention generally relates to monoclonal antibodies that recognize at least one compound from the group consisting of (+) methamphetamine, (+) amphetamine, and (+) 3,4-methylenedioxymethamphetamine ((+) MDMA). Generally speaking, the monoclonal antibodies do not recognize (−) methamphetamine, (−) amphetamine, or (−) MDMA.

17 Claims, 9 Drawing Sheets

(2 of 9 Drawing Sheet(s) Filed in Color)

OTHER PUBLICATIONS

Byrnes-Blake et al, "Pharmacodynamic mechanisms of monoclonal antibody-based antagonism of (+)-methamphetamine in rats", European Journal of Pharmacology, 2003, pp. 119-128, vol. 461.

Byrnes-Blake et al, "Monoclonal IgG affinity and treatment time alters antagonism of (+)-methamphetamine effects in rats", European Journal of Pharmacology, 2005, pp. 86-94, vol. 521.

Chio et al, "Localization of the epitope in methamphetamine and its antibody use for the detection of methamphetamine and benzphetamine by polarization fluoroimmunoassay", Journal of Immunoassy, 1995, pp. 263-278, vol. 16(3).

Cody et al, "Detection of D,L-Amphetamine, D,L-Methamphetamine, and Illicit Amphetamine Analogs Using Diagnostic Products Corporation's Amphetamine and Methamphetamine Radioimmunoassay", Journal of Analytical Toxicology, 1990, pp. 321-324, vol. 14(5).

Colbert et al, "Single-Reagent Polarization Fluoroimmunoassay for Amphetamine in Urine" Clinical Chemistry, 1985, pp. 1193-1195, vol. 31, No. 7.

Cook et al, "Pharmacokinetic of methamphetamine self-administered to human subjects by smoking S-(+)-methamphetamine hydrochloride", Drug Metabolism and Dispositions, 1993, pp. 717-723, vol. 21, No. 4.

Danger et al, "Development of murine monoclonal antibodies to methamphetamine and methamphetamine analogues", Journal of Immunological Methods, 2006, pp. 1-10, vol. 309.

Faraj et al, "Specificity of an Antibody Directed against d-Methamphetamine. Studies with Rigid and Nonrigid Analogs", Journal of Medicinal Chemistry, 1976, pp. 20-25, vol. 19(1).

Farre et al, "Repeated doses administration of MDMA in humans: pharmacological effects and pharmacokinetics", Psychopharmacology, 2004, pp. 364-375, vol. 173.

Hardin et al, "Pharmacodynamics of a Monoclonal Antiphencyclidine Fab with Broad Selectivity for Phencyclidine-Like Drugs", The Journal of Pharmacology and Experimental Therapeutics, 1998, pp. 1113-1122, vol. 285(3).

Kosten et al, "Immunotherapy for the treatment of drug abuse", Pharmacology and Therapeutics, 2005, pp. 76-85 vol. 108.

Laurenzana et al, "Use of Anti-(+)-Methamphetamine Monoclonal Antibody To Significantly Alter (+)-Methamphetamine and (+)-Amphetamine Disposition in Rats", Drug Metabolism and Disposition, 2003, pp. 1320-1326, vol. 31(11).

Li et al, "Four-choice drug discrimination in pigeons", Behavioural Pharmacology, 2001, pp. 621-628, vol. 12.

McMillan et al, "Schedule control of quantal and graded dose-effect curves in a drug-drug-saline discrimination", Pharmacology, Biochemistry and Behavior, 2001, pp. 395-402, vol. 68.

McMillian et al, "Discrimination of pentobarbital doses and drug mixtures under fixed-ratio and fixed-interval reinforcement schedules", Behavioural Pharmacology, 2001, pp. 195-208, vol. 12.

McMillian et al, "Pharmacokinetic antagonism of (+)-methamphetamine discrimination by low-affinity monoclonal anti-methamphetamine antibody", Behavioural Pharmacology, 2002, pp. 465-473, vol. 13.

McMillian et al, "Effects of Murine-Derived Anti-Methamphetamine Monoclonal Antibodies on (+)-Methamphetamine Self-Administration in the Rat", Journal of Pharmacology and Experimental Therapeutics, 2004, pp. 1248-1255, vol. 309(3).

Nam et al, "Production and Characterization of Monoclonal Antibody That Simultaneously Recognizes Methamphetamine and Its Major Metabolite", Biological and Pharmaceutical Bulletin, 1993 pp. 490-492, vol. 16(5).

Owens et al, "Antibodies Against Arylcyclohexylamines and Their Similarities in Binding Specificity with the Phencyclidine Receptor", The Journal of Pharmacology and Experimental Therapeutics, 1998, pp. 472-478 vol. 246(2).

Peterson et al, "Using Hapten Design to Discover Therapeutic Monoclonal Antibodies for Treating Methamphetamine Abuse", Journal of Pharmocology and Experimental Therapeutics, 2007 pp. 30-39, vol. 322(1).

Peterson et al., "Monoclonal Antibody Form and Function: Manufacturing the Right Antibodies for Treating Drug Abuse",The AAPS Journal, 2006, pp. E383-E390, vol. 8(2).

Proksch et al. "Anti-Phencyclidine Monoclonal Antibodies Provide Long-Term Reductions in Brain Phencyclidine Concentrations during Chronic Phencyclidine Administration in Rats", The Journal of Pharmacology and Experimental Therapeutics, 2000, pp. 831-837, vol. 292(3).

Richards et al., "Methamphetamine Abuse and Emergency Department Utilization", West J Med, 1999, pp. 198-202, vol. 170, No. 4.

Riviere et al. "Spontaneous Locomotor Activity and Pharmacokinetics of Intravenous Methamhetamine and Its Metabolite Amphetamine in the Rat", The Journal of Pharmacology and Experimental Therapeutics, 1999, pp. 1220-1226, vol. 291(3).

Riviere et al. "Disposition of Methamphetamine and Its Metabolite Amphetamine in Brain and Other Tissues in Rats after Intravenous Administration", The Journal of Pharmacology and Experimental Therapeutics, 2000, pp. 1042-1047, vol. 292, No. 3.

Suttijitpaisal et al., "Immunoassays of Amphetamines: Immunogen Structure vs Antibody Specificity", Asian Pacific Journal of Allergy and Immunology, 1992, pp. 159-164, vol. 10.

Tempest et al. "Reshaping a Human Monoclonal Antibody to Inhibit Human Respiratory Syncytial Virus Infection in VIVO", Biotechnology, 1991, pp. 266-271, vol. 9.

Terazawa et al., "Development of Monoclonal Antibodies Reactive With Methamphetamine Raised Against a New Antigen", Journal of Immunoassay, 1991, pp. 277-292, vol. 12(2).

Tokura et al., "Induction of Methamphetamine-Specific Antibody Using Biodegradable Carboxymethy-chitin", Analytical Biochemistry, 1987, pp. 117-122, vol. 161.

Usagawa et al. "Preparation of monoclonal antibodies against methamphetamine" Journal of Immunology Methods, 1989, pp. 111-115, vol. 119.

Ward et al. "Radioimmunoassy for the Dual Detection of Amphetamine and Methamphetamine" Journal of Forensic Science, 1994, pp. 1486-1496, vol. 39(6).

Daniels et al, "Effects of anti-phencyclidine and anti-(+)-methamphetamine monoclonal antibodies alone and in combination on the discrimination of phencyclidine and (+)-methamphetamine by pigeons", Psychopharmacology, 2006, pp. 36-44, vol. 185.

Gentry et al, "Safety and efficiency of an anti-(+)-methamphetamine monoclonal antibody in the protection against cardiovascular and central nervous system effects of (+)-methamphetamine in rats", International Immunopharmacology, 2006, pp. 968-977, vol. 6.

Niwaguchi et al, "Determination of d-Methamphetamine in Urine After Administration of d- or dl-Methamphetamine to Rats by Radioimmunoassay Using Optically Sensitive Antiserum", Journal of Forensic Sciences, 1982, pp. 592-597, vol. 27, No. 3.

Pitas et al, "Anti-Phencyclidine Monoclonal Antibody Binding Capacity is not the Only Determinant of Effectiveness, Disproving the Concept that Antibody Capacity is Easily Surmounted", American Society for Pharmacology and Experimental Therapeutics, 2006, pp. 906-912, vol. 34, No. 6.

Valentine et al, "Anti-phencyclidine Monoclonal Fab Fragments Markedly Alter Phencyclidine Pharmacokinetics in Rats", Journal of Pharmacology and Experimental Therapeutics, 1994, pp. 1079-1085, vol. 269(3).

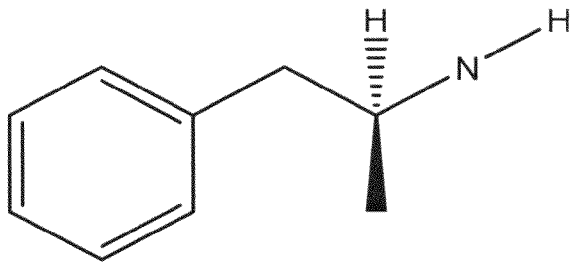
(+) Amphetamine
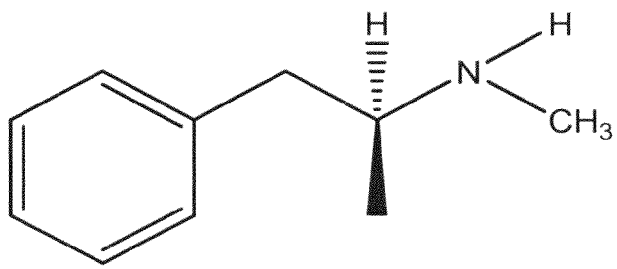
(+) Methamphetamine
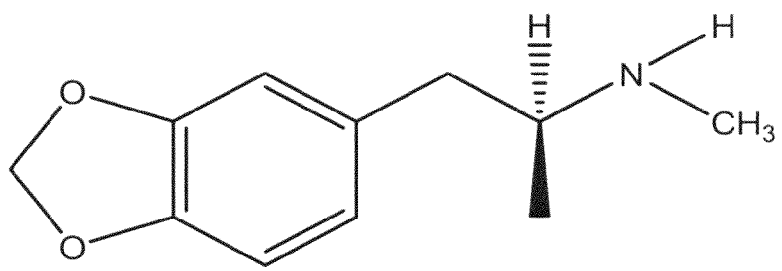
(+)-3,4-Methylenedioxymethamphetamine
FIG. 1

| mAb name | KD (nM) | FR1 | CDR H1 | FR2 | CDR H2 | FR3 | CDR H3 | FR4 | |
|---|---|---|---|---|---|---|---|---|---|
| 6H8 | 250 | QVQLQQPGAELVKPGASMKLSCKASGYTFT | SFWMH | WVKQRPGQGLEWIGE | INPSNGRNKYNEKFKNKATLTVDKSSSTAYMQLSSLTSEDSAVYYC | TRDSF | GGSYDGFYSMDY | WGQGTSVTVS | SEQ. ID NO. 9 |
| 6H4 | 10 | EVQLQESGPSLVKPSQTLSLTCSVTGDSVT | SGYWS | WIRQFPGNKLDYMGY | IS-YRGSTYYNPSLKSRISITRDTSKNQVYLQLKSVSSEDTATYYC | SYFDS | DD-YAMEY-- | WGQGTSVTVS | SEQ. ID NO. 10 |
| 6H7 | 41 | DVKLQESGPGLVKPSQSLSLTCSVTGSSIT | SAYYWNWN | RQFPGNKLEWMGY | IRYDGYNN-YNPSLKNRISITRDTSKNQFFLKLNSVTTEDTATYYC | ARDDY | DEAY---- | WGQGTLVTVS | SEQ. ID NO. 11 |
| 9B11 | 41 | EVQLPESGPGLVAPSQSLSITCTVSGFSLT | DGYGVNW | VRQPPGKGLEWLGM | IW-DDGDTDYSSVLKSRLSITKDNSKNQVFLKMNRLQTDDTARYFC | ARDTL | YTSYAMDY-- | WGQGTSVTVS | SEQ. ID NO. 12 |
| 4G9 | 40 | EYQLQQSGTVLARPGASVKMSCKASGYTFT | SYWMH | WVKQRPGQGLEWIGG | IYPGNSDTTYNQKFKGKAKLTAVTSTSTAYMELSSLTNEDSAVYYC | LYGNY | DFDY---- | WGQGTTLTVS | SEQ. ID NO. 13 |

FR1 (positions 1–23)

| | 1 2 3 4 5 6 7 8 9 10 11 12 13 14 15 16 17 18 19 20 21 22 23 |
|---|---|
| 6H8 (250) | Q I V L T Q S P A I M S A S P G E K V T I S C |
| 6H4 (10) | Q I V L T Q S P A I M S A S P G E K V T L T C |
| 6H7 (41) | Q I V L T Q S P A I M S A S P G E K V T L T C |
| 9B11 (41) | Q A V V T Q E S A - L T T S P G E T V T L T C |
| 4G9 (40) | D V Q M T Q S P S S L S A S L G G K V T I T C |

CDR L1 / FR2 / CDR L2 / FR3 (positions 24–71)

| | 24 25 26 27 27A 27B 27C 28 29 30 31 32 33 34 35 | 36 37 38 39 40 41 42 43 44 45 46 47 48 49 | 50 51 52 53 54 55 56 | 57 58 59 60 61 62 63 64 65 66 67 68 69 70 71 |
|---|---|---|---|---|
| 6H8 (250) | S A S S S - - V S - - Y M Y W | Y Q Q K P G S S P K P W I | Y R T S I L A | S G V P A R F S G S G S G T S Y |
| 6H4 (10) | S A S S S - - V S - - V S Y W | Y Q Q K P G S S P K L W I | Y S T S N L A | S G V P A R F S G S G S G T S Y |
| 6H7 (41) | S A S S S V R S S Y L Y - - W | Y Q Q K P G S S P K L W I | Y S T S N L A | S G V P A R F S G S G S G T F Y |
| 9B11 (41) | R S S A G A V T A S N Y A N W | V Q E K P D H L F T G L I | G G T N I R A | P G I P A R F S G S G S L I G D K A |
| 4G9 (40) | K A S Q D - I N K F I A - - W | Y Q H K P G K G P R L L I | H Y T S T L Q | P G I P S R F S G S G S G R D Y |

FR3 / CDR L3 / FR4 (positions 72–108)

| | 72 73 74 75 76 77 78 79 80 81 82 83 84 85 86 87 88 | 89 90 91 92 93 94 95 95A 96 97 | 98 99 100 101 102 103 104 105 106 106A 107 108 | |
|---|---|---|---|---|
| 6H8 (250) | S L T I I N M E A E D A A T Y Y C | Q H Y H S Y P - L T | F G A G T K L E L K R A | SEQ. ID NO. 14 |
| 6H4 (10) | S L T I S S M E A E D A A S Y F C | H Q W S S F P - F T | F G S G T K L E I K R A | SEQ. ID NO. 15 |
| 6H7 (41) | S L T I S S M E A E D A A S Y F C | H Q W S S Y P - Y T | F G G G T K L E I K R A | SEQ. ID NO. 16 |
| 9B11 (41) | A L T I T G A Q T E D E A I Y F C | V L W F S N H S V - | F G G G T K L T V L G L | SEQ. ID NO. 17 |
| 4G9 (40) | S F S I S N L E P E D I A T Y Y C | L Q Y A N L L P W T | F G G G T K L E I K R A | SEQ. ID NO. 18 |

| mAb Name | CDR Regions and RMSD (Å) from mAb6H4 | | | | | |
|---|---|---|---|---|---|---|
|  | L1 | L2 | L3 | H1 | H2 | H3 |
| mAb6H8 | 2.27 | 0.84 | 0.67 | 1.85 | 3.36 | 6.67 |
| mAb4G9 | 2.44 | 0.88 | 3.72 | 1.39 | 3.59 | 7.22 |

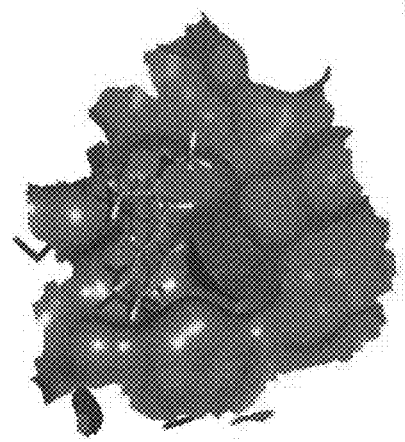
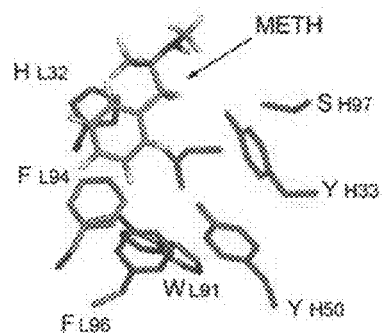
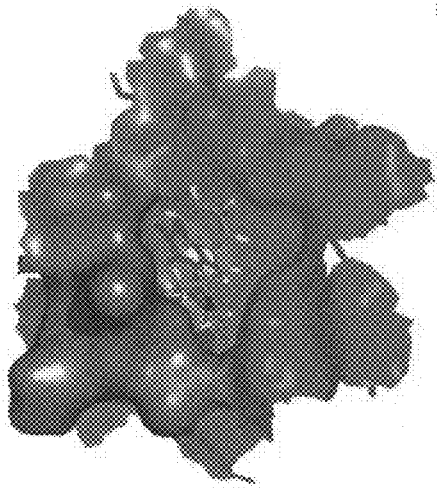
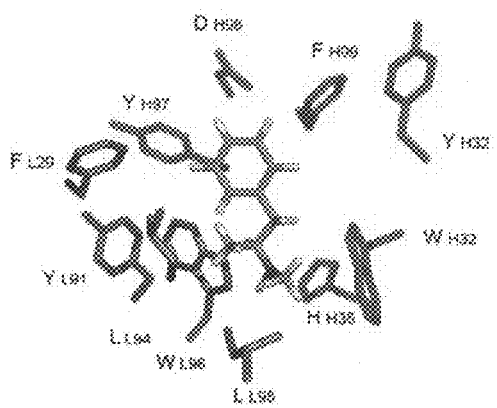
FIG. 4

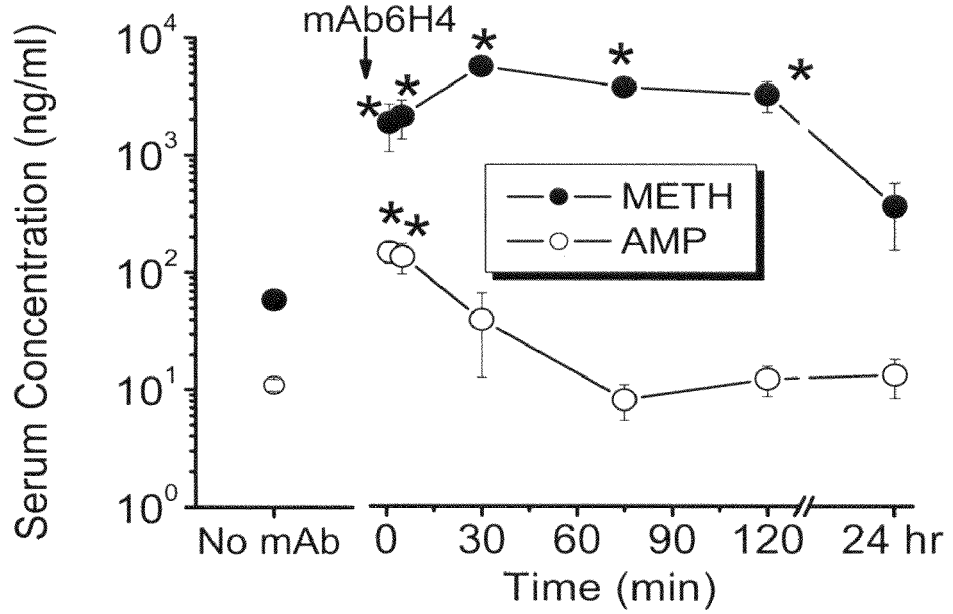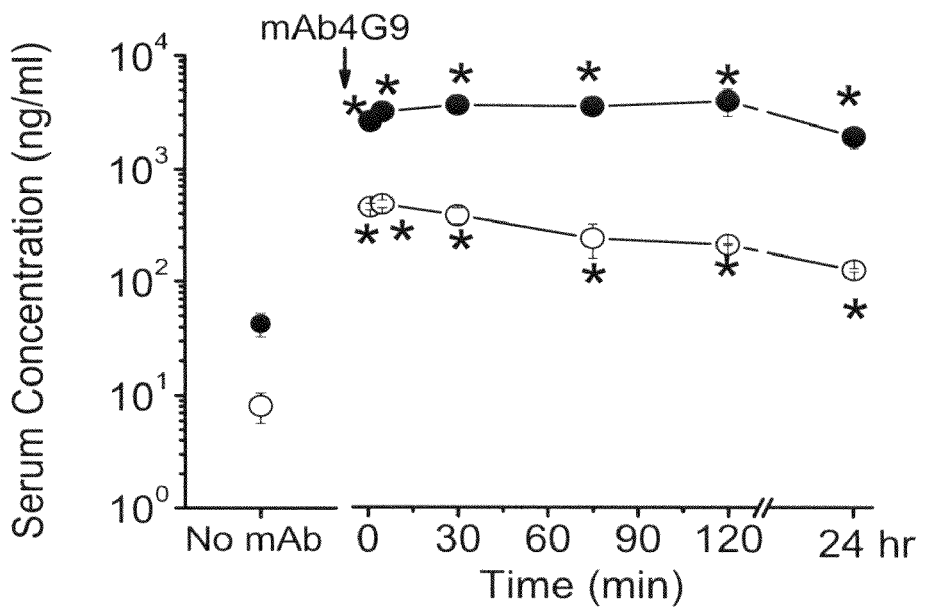
FIG. 7

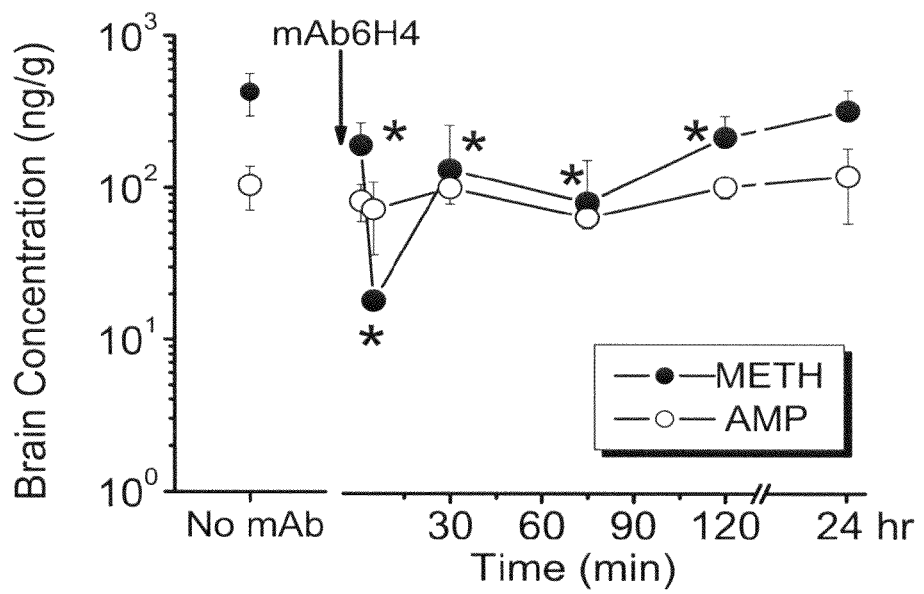
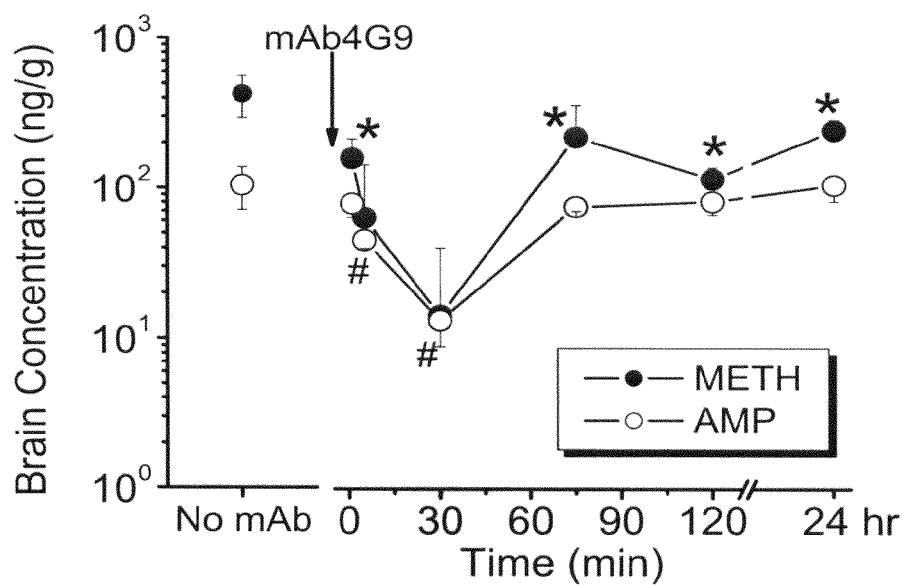
FIG. 8

SEQUENCE LISTING

<160> NUMBER OF SEQ ID NOS: 26

<210> SEQ ID NO 1
<211> LENGTH: 36
<212> TYPE: DNA
<213> ORGANISM: Artificial
<220> FEATURE:
<223> OTHER INFORMATION: MOUSE

<400> SEQUENCE: 1
ggggcggccg cgcgtctcag gacctttgtc tctaac                              36

<210> SEQ ID NO 2
<211> LENGTH: 40
<212> TYPE: DNA
<213> ORGANISM: Artificial
<220> FEATURE:
<223> OTHER INFORMATION: MOUSE

<400> SEQUENCE: 2
atggcctgga tcttcactta tactctctct cctggctctc                          40

<210> SEQ ID NO 3
<211> LENGTH: 38
<212> TYPE: DNA
<213> ORGANISM: Artificial
<220> FEATURE:
<223> OTHER INFORMATION: MOUSE

<400> SEQUENCE: 3
ggggcggccg cagggctcca aggacactgg gatcattt                            38

<210> SEQ ID NO 4
<211> LENGTH: 22
<212> TYPE: DNA
<213> ORGANISM: Artificial
<220> FEATURE:
<223> OTHER INFORMATION: MOUSE

<400> SEQUENCE: 4
ctcccggtct ccgggtaaat ga                                             22

<210> SEQ ID NO 5
<211> LENGTH: 29
<212> TYPE: DNA
<213> ORGANISM: Artificial
<220> FEATURE:
<223> OTHER INFORMATION: MOUSE

<400> SEQUENCE: 5
gagtgcagct tcaggagtca ggacctagc                                      29

<210> SEQ ID NO 6
<211> LENGTH: 50
<212> TYPE: DNA
<213> ORGANISM: Artificial
<220> FEATURE:
<223> OTHER INFORMATION: MOUSE

<400> SEQUENCE: 6
gatgtaaaac ttcaggagtc aggacctggc ctcgtgaaac cttctcagtc               50

<210> SEQ ID NO 7
<211> LENGTH: 30
<212> TYPE: DNA

-continued

```
<213> ORGANISM: Artificial
<220> FEATURE:
<223> OTHER INFORMATION: MOUSE

<400> SEQUENCE: 7
gaggtgcagc ttccggagtc aggacctagc                                        30

<210> SEQ ID NO 8
<211> LENGTH: 26
<212> TYPE: DNA
<213> ORGANISM: Artificial
<220> FEATURE:
<223> OTHER INFORMATION: MOUSE

<400> SEQUENCE: 8
gagtaccagc tccagcagtc tgggac                                            26

<210> SEQ ID NO 9
<211> LENGTH: 123
<212> TYPE: PRT
<213> ORGANISM: Mus musculus

<400> SEQUENCE: 9
```

Gln Val Gln Leu Gln Gln Pro Gly Ala Glu Leu Val Lys Pro Gly Ala
1               5                   10                  15

Ser Met Lys Leu Ser Cys Lys Ala Ser Gly Tyr Thr Phe Thr Ser Phe
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Asn Lys Tyr Asn Glu Lys Phe
    50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Ser Phe Gly Gly Ser Tyr Asp Gly Phe Tyr Ser Met Asp
            100                 105                 110

Tyr Trp Gly Gln Gly Thr Ser Val Thr Val Ser
        115                 120

```
<210> SEQ ID NO 10
<211> LENGTH: 117
<212> TYPE: PRT
<213> ORGANISM: Mus musculus

<400> SEQUENCE: 10
```

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Ser Trp Ile Arg Gln Phe Pro Gly Asn Lys Leu Asp Tyr Met
        35                  40                  45

Gly Tyr Ile Ser Tyr Arg Gly Ser Thr Tyr Tyr Asn Pro Ser Leu Lys
    50                  55                  60

Ser Arg Ile Ser Ile Thr Arg Asp Thr Ser Lys Asn Gln Val Tyr Leu
65                  70                  75                  80

Gln Leu Lys Ser Val Ser Ser Glu Asp Thr Ala Thr Tyr Tyr Cys Ser
                85                  90                  95

Tyr Phe Asp Ser Asp Asp Tyr Ala Met Glu Tyr Trp Gly Gln Gly Thr
            100                 105                 110

```
Ser Val Thr Val Ser
        115

<210> SEQ ID NO 11
<211> LENGTH: 115
<212> TYPE: PRT
<213> ORGANISM: Mus musculus

<400> SEQUENCE: 11

Asp Val Lys Leu Gln Glu Ser Gly Pro Gly Leu Val Lys Pro Ser Gln
1               5                   10                  15

Ser Leu Ser Leu Thr Cys Ser Val Thr Gly Ser Ser Ile Thr Ser Ala
            20                  25                  30

Tyr Tyr Trp Asn Trp Asn Arg Gln Phe Pro Gly Asn Lys Leu Glu Trp
        35                  40                  45

Met Gly Tyr Ile Arg Tyr Asp Gly Tyr Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Asp Asp Tyr Asp Glu Ala Tyr Trp Gly Gln Gly Thr Leu Val
            100                 105                 110

Thr Val Ser
        115

<210> SEQ ID NO 12
<211> LENGTH: 119
<212> TYPE: PRT
<213> ORGANISM: Mus musculus

<400> SEQUENCE: 12

Glu Val Gln Leu Pro Glu Ser Gly Pro Gly Leu Val Ala Pro Ser Gln
1               5                   10                  15

Ser Leu Ser Ile Thr Cys Thr Val Ser Gly Phe Ser Leu Thr Asp Gly
            20                  25                  30

Tyr Gly Val Asn Trp Val Arg Gln Pro Pro Gly Lys Gly Leu Glu Trp
        35                  40                  45

Leu Gly Met Ile Trp Asp Asp Gly Asp Thr Asp Tyr Ser Ser Val Leu
    50                  55                  60

Lys Ser Arg Leu Ser Ile Thr Lys Asp Asn Ser Lys Asn Gln Val Phe
65                  70                  75                  80

Leu Lys Met Asn Arg Leu Gln Thr Asp Thr Ala Arg Tyr Phe Cys
                85                  90                  95

Ala Arg Asp Thr Leu Tyr Thr Ser Tyr Ala Met Asp Tyr Trp Gly Gln
            100                 105                 110

Gly Thr Ser Val Thr Val Ser
        115

<210> SEQ ID NO 13
<211> LENGTH: 115
<212> TYPE: PRT
<213> ORGANISM: Mus musculus

<400> SEQUENCE: 13

Glu Tyr Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
```

-continued

```
                     20                  25                  30
Trp Met His Trp Val Lys Gln Arg Pro Gly Gln Gly Leu Glu Trp Ile
         35                  40                  45
Gly Gly Ile Tyr Pro Gly Asn Ser Asp Thr Thr Tyr Asn Gln Lys Phe
     50                  55                  60
Lys Gly Lys Ala Lys Leu Thr Ala Val Thr Ser Thr Ser Thr Ala Tyr
 65                  70                  75                  80
Met Glu Leu Ser Ser Leu Thr Asn Glu Asp Ser Ala Val Tyr Tyr Cys
                 85                  90                  95
Leu Tyr Gly Asn Tyr Asp Phe Asp Tyr Trp Gly Gln Gly Thr Thr Leu
            100                 105                 110
Thr Val Ser
        115

<210> SEQ ID NO 14
<211> LENGTH: 108
<212> TYPE: PRT
<213> ORGANISM: Mus musculus

<400> SEQUENCE: 14

Gln Ile Val Leu Thr Gln Ser Pro Ala Ile Met Ser Ala Ser Pro Gly
  1               5                  10                  15
Glu Lys Val Thr Ile Ser Cys Ser Ala Ser Ser Ser Val Ser Tyr Met
                 20                  25                  30
Tyr Trp Tyr Gln Gln Lys Pro Gly Ser Ser Pro Lys Pro Trp Ile Tyr
             35                  40                  45
Arg Thr Ser Ile Leu Ala Ser Gly Val Pro Ala Arg Phe Ser Gly Ser
     50                  55                  60
Gly Ser Gly Thr Ser Tyr Ser Leu Thr Ile Ile Asn Met Glu Ala Glu
 65                  70                  75                  80
Asp Ala Ala Thr Tyr Tyr Cys Gln His Tyr His Ser Tyr Pro Leu Thr
                 85                  90                  95
Phe Gly Ala Gly Thr Lys Leu Glu Leu Lys Arg Ala
            100                 105

<210> SEQ ID NO 15
<211> LENGTH: 110
<212> TYPE: PRT
<213> ORGANISM: Mus musculus

<400> SEQUENCE: 15

Gln Ile Val Leu Thr Gln Ser Pro Ala Ile Met Ser Ala Ser Pro Gly
  1               5                  10                  15
Glu Lys Val Thr Leu Thr Cys Ser Ala Ser Ser Ser Val Ser Ser Ser
                 20                  25                  30
His Leu Tyr Trp Tyr Gln Gln Lys Pro Gly Ser Ser Pro Lys Leu Trp
             35                  40                  45
Ile Tyr Ser Thr Ser Asn Leu Ala Ser Gly Val Pro Ala Arg Phe Ser
     50                  55                  60
Gly Ser Gly Ser Gly Thr Ser Tyr Ser Leu Thr Ile Ser Ser Met Glu
 65                  70                  75                  80
Ala Glu Asp Ala Ala Ser Tyr Phe Cys His Gln Trp Ser Ser Phe Pro
                 85                  90                  95
Phe Thr Phe Gly Ser Gly Thr Lys Leu Glu Ile Lys Arg Ala
            100                 105                 110

<210> SEQ ID NO 16
```

```
<211> LENGTH: 110
<212> TYPE: PRT
<213> ORGANISM: Mus musculus

<400> SEQUENCE: 16

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Arg Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
50                  55                  60

Gly Ser Gly Ser Gly Thr Phe Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys Arg Ala
            100                 105                 110

<210> SEQ ID NO 17
<211> LENGTH: 111
<212> TYPE: PRT
<213> ORGANISM: Mus musculus

<400> SEQUENCE: 17

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Ala Ser
            20                  25                  30

Asn Tyr Ala Asn Trp Val Gln Glu Lys Pro Asp His Leu Phe Thr Gly
        35                  40                  45

Leu Ile Gly Gly Thr Asn Ile Arg Ala Pro Gly Ile Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Phe Ser Asn
                85                  90                  95

His Ser Val Phe Gly Gly Gly Thr Lys Leu Thr Val Leu Gly Leu
            100                 105                 110

<210> SEQ ID NO 18
<211> LENGTH: 110
<212> TYPE: PRT
<213> ORGANISM: Mus musculus

<400> SEQUENCE: 18

Asp Val Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Ala Asn Leu Leu Pro
```

```
                           85                  90                  95
Trp Thr Phe Gly Gly Gly Thr Lys Leu Glu Ile Lys Arg Ala
                100                 105                 110

<210> SEQ ID NO 19
<211> LENGTH: 446
<212> TYPE: PRT
<213> ORGANISM: Mus musculus

<400> SEQUENCE: 19

Glu Tyr Gln Leu Gln Gln Ser Gly Thr Val Leu Ala Arg Pro Gly Ala
 1               5                  10                  15

Ser Val Lys Met Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Gly Ile Tyr Pro Gly Asn Ser Asp Thr Thr Tyr Asn Gln Lys Phe
        50                  55                  60

Lys Gly Lys Ala Lys Leu Thr Ala Val Thr Ser Thr Ser Thr Ala Tyr
 65                  70                  75                  80

Met Glu Leu Ser Ser Leu Thr Asn Glu Asp Ser Ala Val Tyr Tyr Cys
                 85                 90                  95

Leu Tyr Gly Asn Tyr Asp Phe Asp Tyr Trp Gly Gln Gly Thr Thr Leu
                100                 105                 110

Thr Val Ser Ser Ala Lys Thr Thr Ala Pro Ser Val Tyr Pro Leu Ala
                115                 120                 125

Pro Val Cys Gly Asp Thr Thr Gly Ser Ser Val Thr Leu Gly Cys Leu
        130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
                180                 185                 190

Ser Gln Ser Ile Thr Cys Asn Val Ala His Pro Ala Ser Ser Thr Lys
            195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
                260                 265                 270

Gln Ile Ser Trp Phe Val Asn Asn Val Glu Val His Thr Ala Gln Thr
            275                 280                 285

Gln Thr His Arg Glu Asp Tyr Asn Ser Thr Leu Arg Val Val Ser Ala
        290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
                340                 345                 350

Pro Glu Glu Glu Met Thr Lys Lys Gln Val Thr Leu Thr Cys Met Val
```

```
                    355                 360                 365
Thr Asp Phe Met Pro Glu Asp Ile Tyr Val Glu Trp Thr Asn Asn Gly
                370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
                420                 425                 430

Asn His His Thr Thr Lys Ser Phe Ser Arg Thr Pro Gly Lys
                435                 440                 445

<210> SEQ ID NO 20
<211> LENGTH: 1341
<212> TYPE: DNA
<213> ORGANISM: Mus musculus

<400> SEQUENCE: 20
gagtatcagc tgcagcagtc tgggactgtg ctggcaaggc cgggggcttc agtgaagatg      60
tcctgcaagg cctctggcta cacctttacc aactactgga tgcactgggt aaaacagagg     120
cctggacagg gtctggaatg gattggcggt atttatcctg gaaatagtga tactacctac    180
aaccagaagt tcaagggcaa ggccaaactg actgcagtca catccaccag cactgcctac    240
atggagctca gcagcctgac aaatgaggac tctgcggtct attactgtct atatggtaac    300
tacgactttg actactgggg ccaaggcacc actctcacag tctcctcagc aaaacaaca    360 gccccatcgg tctatccact ggcccctgtg tgtggagata caactggctc ctcggtgact     420
ctaggatgcc tggtcaaggg ttatttccct gagccagtga ccttgacctg aactctgga    480 tccctgtcca gtggtgtgca ccttcccca gctgtcctgc agtctgacct ctacaccctc     540
agcagctcag tgactgtaac ctcgagcacc tggcccagcc agtccatcac ctgcaatgtg    600
gcccacccgg caagcagcac caaggtggac aagaaaattg agcccagagg gcccacaatc    660
aagccctgtc ctccatgcaa atgcccagca cctaacctct gggtggacc atccgtcttc    720 atcttccctc caaagatcaa ggatgtactc atgatctccc tgagccccat agtcacatgt    780
gtggtggtgg atgtgagcga ggatgaccca gatgtccaga tcagctggtt tgtgaacaac    840
gtggaagtac acacagctca gacacaaacc catagagagg attacaacag tactctccgg    900
gtggtcagtg ccctccccat ccagcaccag gactggatga gtggcaagga gttcaaatgc    960
aaggtcaaca acaaagacct cccagcgccc atcgagagaa ccatctcaaa acccaaaggg    1020
tcagtaagag ctccacaggt atatgtcttg cctccaccag aagaagagat gactaagaaa    1080
caggtcactc tgacctgcat ggtcacagac ttcatgcctg aagacattta cgtggagtgg   1140
accaacaacg ggaaaacaga gctaaactac aagaacactg aaccagtcct ggactctgat    1200
ggttcttact tcatgtacag caagctgaga gtggaaaaga gaactgggt ggaaagaaat    1260 agctactcct gttcagtggt ccacgagggt ctgcacaatc accacgac taagagcttc    1320 tcccggactc cgggtaaatg a                                              1341

<210> SEQ ID NO 21
<211> LENGTH: 215
<212> TYPE: PRT
<213> ORGANISM: Mus musculus

<400> SEQUENCE: 21

Asp Ile Gln Met Thr Gln Ser Pro Ser Ser Leu Ser Ala Ser Leu Gly
```

```
             1               5                  10                 15
Gly Lys Val Thr Ile Thr Cys Lys Ala Ser His Asp Val Asn Lys Phe
                    20                  25                  30

Ile Ala Trp Tyr Gln His Lys Pro Gly Lys Gly Pro Arg Leu Leu Ile
                35                  40                  45

His Tyr Thr Ser Thr Leu Gln Pro Gly Ile Pro Ser Arg Phe Ser Gly
            50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Thr Asn Leu Leu Pro
                85                  90                  95

Trp Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
            195                 200                 205

Ser Phe Asn Arg Asn Glu Cys
            210                 215

<210> SEQ ID NO 22
<211> LENGTH: 648
<212> TYPE: DNA
<213> ORGANISM: Mus musculus

<400> SEQUENCE: 22
gacatccaga tgacccagtc tccatcctca ctgtctgcat ctctgggagg caaagtcacc      60
atcacttgca aggcaagcca tgacgttaac aagtttatag cttggtacca acacaagcct    120
ggaaaaggtc ctaggctgct catacattac acatctacat tacagccagg catcccatcg    180
aggttcagtg gcagtgggtc tgggagagat tattccttca gcatcagcaa cctggaacct    240
gaagatattg caacttatta ttgtctacag tatactaatc ttctaccgtg gacgttcggt    300
ggaggcacca agctggaaat caaacgggct gatgctgcac caactgtatc catcttccca    360
ccatccagtg agcagttaac atctggaggt gcctcagtcg tgtgcttctt gaacaacttc    420
taccccaaag acatcaatgt caagtggaag attgatggca gtgaacgaca aaatggcgtc    480
ctgaacagtt ggactgatca ggacagcaaa gacagcacct acagcatgag cagcaccctc    540
acgttgacca aggacgagta tgaacgacat aacagctata cctgtgaggc cactcacaag    600
acatcaactt cacccattgt caagagcttc aacaggaatg agtgttag                 648

<210> SEQ ID NO 23
<211> LENGTH: 1359
<212> TYPE: DNA
<213> ORGANISM: Mus musculus

<400> SEQUENCE: 23
gagtaccagc tccagcagtc tgggactgtg ctggcaaggc cgggggcttc agtgaagatg      60
```

```
tcctgcaagg cctctggcta cacctttacc agctactgga tgcactgggt aaaacagagg    120
cctggacagg gtctggaatg gattggcggt atttatcctg gaaatagtga tactacctac    180
aaccagaagt tcaagggcaa ggccaaactg actgcagtca catccaccag cactgcctac    240
atggagctca gcagcctgac aaatgaggac tctgcggtct attactgtct atatggtaac    300
tacgactttg actactgggg ccaaggcacc actctcacag tctcctcagc aaaacaaca    360 cccccatcag tctatccact ggcccctggg tgtggagata caactggttc ctccgtgact    420
ctgggatgcc tggtcaaggg ctacttccct gagtcagtga ctgtgacttg aactctgga    480 tccctgtcca gcagtgtgca caccttccca gctctcctgc agtctggact ctacactatg    540
agcagctcag tgactgtccc ctccagcacc tggccaagtc agaccgtcac ctgcagcgtt    600
gctcacccag ccagcagcac cacggtggac aaaaaacttg agcccagcgg gcccatttca    660
acaatcaacc cctgtcctcc atgcaaggag tgtcacaaat gcccagctcc taacctcgag    720
ggtggaccat ccgtcttcat cttccctcca aatatcaagg atgtactcat gatctccctg    780
acacccaagg tcacgtgtgt ggtggtggat gtgagcgagg atgacccaga cgtccagatc    840
agctggtttg tgaacaacgt ggaagtacac acagctcaga cacaaaccca tagagaggat    900
tacaacagta ctatccgggt ggtcagcacc ctcccccatcc agcaccagga ctggatgagt    960
ggcaaggagt tcaaatgcaa ggtcaacaac aaagacctcc catcacccat cgagagaacc   1020
atctcaaaaa ttaaagggct agtcagagct ccacaagtat acatcttgcc gccaccagca   1080
gagcagttgt ccaggaaaga tgtcagtctc acttgcctgg tcgtgggctt caaccctgga   1140
gacatcagtg tggagtggac cagcaatggg catacagagg agaactacaa ggacaccgca   1200
ccagtcttgg actctgacgg ttcttacttc atatatagca agctcaatat gaaaacaagc   1260
aagtgggaga aaacagattc cttctcatgc aacgtgagac acgagggtct gaaaaattac   1320
tacctgaaga gaccatctc ccggtctccg ggtaaatga                          1359

<210> SEQ ID NO 24
<211> LENGTH: 648
<212> TYPE: DNA
<213> ORGANISM: Mus musculus

<400> SEQUENCE: 24
gacgtccaga tgacacagtc tccatcctcg ctgtctgcat ctctgggagg caaagtcacc    60
atcacttgca aggcaagcca agacattaac aagtttatag cttggtacca acacaagcct   120
ggaaaaggtc ctaggctgct catacattac acatctacat tacagccagg catcccatcg   180
aggttcagtg aagtgggtc tgggagagat tattccttca gcatcagcaa cctggaacct   240
gaagatattg caacttatta ttgtctacag tatgctaatc ttctaccgtg acgttcggt    300 ggaggcacca agctggaaat caaacgggct gatgctgcac caactgtatc catcttccca   360
ccatccagtg agcagttaac atctggaggt gcctcagtcg tgtgcttctt gaacaacttc   420
taccccaaag acatcaatgt caagtggaag attgatggca gtgaacgaca aaatggcgtc   480
ctgaacagtt ggactgatca ggacagcaaa gacagcacct acagcatgag cagcaccctc   540
acgttgacca aggacgagta tgaacgacat aacagctata cctgtgaggc cactcacaag   600
acatcaactt cacccattgt caagagcttc aacaggaatg agtgttag                648

<210> SEQ ID NO 25
<211> LENGTH: 452
<212> TYPE: PRT
<213> ORGANISM: Mus musculus
```

<400> SEQUENCE: 25

```
Glu Tyr Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Gly Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Leu Tyr Gly Asn Tyr Asp Phe Asp Tyr Trp Gly Gln Gly Thr Thr Leu
            100                 105                 110

Thr Val Ser Ser Ala Lys Thr Thr Pro Pro Ser Val Tyr Pro Leu Ala
        115                 120                 125

Pro Gly Cys Gly Asp Thr Thr Gly Ser Ser Val Thr Leu Gly Cys Leu
    130                 135                 140

Val Lys Gly Tyr Phe Pro Glu Ser Val Thr Val Thr Trp Asn Ser Gly
145                 150                 155                 160

Ser Leu Ser Ser Ser Val His Thr Phe Pro Ala Leu Leu Gln Ser Gly
                165                 170                 175

Leu Tyr Thr Met Ser Ser Ser Val Thr Val Pro Ser Ser Thr Trp Pro
            180                 185                 190

Ser Gln Thr Val Thr Cys Ser Val Ala His Pro Ala Ser Ser Thr Thr
        195                 200                 205

Val Asp Lys Lys Leu Glu Pro Ser Gly Pro Ile Ser Thr Ile Asn Pro
    210                 215                 220

Cys Pro Pro Cys Lys Glu Cys His Lys Cys Pro Ala Pro Asn Leu Glu
225                 230                 235                 240

Gly Gly Pro Ser Val Phe Ile Phe Pro Pro Asn Ile Lys Asp Val Leu
                245                 250                 255

Met Ile Ser Leu Thr Pro Lys Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Ile Arg Val Val Ser Thr Leu Pro Ile Gln His Gln Asp Trp Met Ser
305                 310                 315                 320

Gly Lys Glu Phe Lys Cys Lys Val Asn Asn Lys Asp Leu Pro Ser Pro
                325                 330                 335

Ile Glu Arg Thr Ile Ser Lys Ile Lys Gly Leu Val Arg Ala Pro Gln
            340                 345                 350

Val Tyr Ile Leu Pro Pro Ala Glu Gln Leu Ser Arg Lys Asp Val
        355                 360                 365

Ser Leu Thr Cys Leu Val Val Gly Phe Asn Pro Gly Asp Ile Ser Val
    370                 375                 380

Glu Trp Thr Ser Asn Gly His Thr Glu Glu Asn Tyr Lys Asp Thr Ala
385                 390                 395                 400

Pro Val Leu Asp Ser Asp Gly Ser Tyr Phe Ile Tyr Ser Lys Leu Asn
                405                 410                 415
```

```
Met Lys Thr Ser Lys Trp Glu Lys Thr Asp Ser Phe Ser Cys Asn Val
            420                 425                 430

Arg His Glu Gly Leu Lys Asn Tyr Tyr Leu Lys Lys Thr Ile Ser Arg
            435                 440                 445

Ser Pro Gly Lys
        450

<210> SEQ ID NO 26
<211> LENGTH: 215
<212> TYPE: PRT
<213> ORGANISM: Mus musculus

<400> SEQUENCE: 26

Asp Val Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65              70                  75                  80

Glu Asp Ile Ala Thr Tyr Tyr Cys Leu Gln Tyr Ala Asn Leu Leu Pro
                85                  90                  95

Trp Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145             150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

MONOCLONAL ANTIBODIES THAT SELECTIVELY RECOGNIZE METHAMPHETAMINE AND METHAMPHETAMINE LIKE COMPOUNDS

CROSS REFERENCE TO RELATED APPLICATIONS

This application claims priority to U.S. Provisional Application Ser. No. 60/813,917, filed Jun. 15, 2006, and U.S. Provisional Application Ser. No. 60/913,124, filed Apr. 20, 2007, each of which is hereby incorporated by reference in their entirety.

GOVERNMENTAL RIGHTS

This invention was made with government support under DA11560, DA14361, and DA05477 awarded by the National Institute on Drug Abuse. The government has certain rights in the invention.

FIELD OF THE INVENTION

The invention provides monoclonal antibodies that recognize (+)methamphetamine, (+)amphetamine, and/or (+)3,4-methylenedioxymethamphetamine ((+)MDMA), but typically do not recognize (−)methamphetamine, (−)amphetamine, or (−)MDMA.

BACKGROUND OF THE INVENTION (+)Methamphetamine ((+)METH) abuse has become America's number one drug threat (NACO, 2005). Known strategies for combating (+)methamphetamine drug use all have drawbacks. Current pharmacotherapies for managing the acute cardiovascular system, central nervous system and toxic effects are mostly supportive (Sato, 1992; Albertson et al., 1999; Richards et al., 1999); and do nothing to remove the drug from its sites of action in the brain. Also lacking are medications that can reduce or treat the medically crippling effects of (+)METH addiction. Antibodies provide an attractive potential medication that can target the drug instead of the site of action (Kosten and Owens, 2005). These high affinity protein-based medications act as so-called pharmacokinetic antagonists, sequestering the drug in the bloodstream away from medically vulnerable tissues like the brain and heart.

Unlike nicotine and cocaine where the effects are caused by a single, specific compound, drugs like opiates (e.g., morphine), arylcyclohexylamines (e.g., phencyclidine) and amphetamines (e.g., (+)METH) are starting structures from which many pharmacologically similar compounds can be synthesized. These so-called "designer drugs" can be chemically modified to alter their effects. Thus, for an antibody to have the broadest medical applicability, it should have high affinity and specificity for more than one medically important member of this drug class (i.e., (+)METH, (+)amphetamine ((+)AMP) and (+)MDMA).

There are other medication design issues that further complicate the development of effective treatments for (+)METH-like stimulants. First, (+)METH is one of several stimulant drugs of abuse with similar or overlapping effects. In particular, (+)AMP is both a pharmacologically active metabolite of (+)METH and a frequently used drug of abuse that could be substituted for (+)METH. Next, (+/−)3,4-methylenedioxymethamphetamine is the racemic mixture commonly referred to as MDMA or ecstasy. The plus isomer ((+)MDMA) has predominately dopaminergic, stimulant-like activity with overlapping effects with (+)METH, while (−)MDMA has predominately serotonergic effects (Cho and Segal, 1994). (+)METH, (+)AMP, and (+)MDMA can produce life threatening effects at high doses (Cho and Segal, 1994; Farre et al., 2004). Additionally, all of these drugs are plus stereoisomers, with the minus isomers having a significantly different pharmacological profile of effects, some of which may be beneficial. For example, (−)methamphetamine is commonly used as a bronchodilator in over the counter medications. The minus isomers of these drugs could potentially be purposely taken by drug abusers to neutralize mAb medications with high affinity binding for both plus and minus stereoisomers. In a related way, there are many structurally similar compounds like ephedrine and pseudoephedrine that could be used to lessen the efficacy of antibodies if the antibody is not highly specific for (+)METH-like structures.

There is a need in the art for specific antibodies that recognize at least one or more of (+)methamphetamine, (+)amphetamine, or (+)MDMA, and that do not substantially cross-react with (−)methamphetamine, (−)amphetamine, or (−)MDMA. In particular, there is a need for specific monoclonal antibodies that recognize each compound of the group consisting of (+)methamphetamine, (+)amphetamine, and (+)MDMA, and that do not substantially cross-react with (−)methamphetamine, (−)amphetamine, or (−)MDMA.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 1 depicts the chemical structures of (+)methamphetamine, (+)amphetamine, and (+)3,4-methylenedioxymethamphetamine ((+)MDMA).

FIG. 2 presents amino acid sequence alignments of the variable regions of five moderate to high affinity anti-(+)METH and anti-(+)METH/(+)AMP, and anti-(+)METH/(+)AMP/(+)MDMA mAb (herein, mAb refers to monoclonal antibodies, both singular and plural). Panel A presents the amino acid sequences of the heavy chains. Panel B presents the amino acid sequences of the light chains. The sequences are presented in single letter amino acid notation and numbered according to Kabat and Wu (1991 J Immunol 147:1709-1719). Location of the framework (FR) and complementarily determining region (CDR) residues are indicated for the heavy chains and light chains.

FIG. 4 illustrates modeled structures of the anti-(+)METH mAb variable chains. In this model, METH (magenta) has been computationally docked into a pocket at the interface of the VH and VL chains with FlexX software. Left panels: Surface rendering of deep pocket in mAb6H4 and mAb4G9. The VL chain domain is on the left side in blue and the VH chain domain is on the right in green. Right panels: Stick representation of mAb6H4 and mAb4G9. Only side chains within 8 angstroms of the METH molecule are shown for clarity. The view is oriented in a "top view" with the same color scheme as in left panel. The side chains are labeled and numbered in the Kabat scheme as in FIG. 2.

FIG. 7 depicts two graphs showing the effect of mAb6H4 (Panel A) and mAb4G9 (Panel B) on METH (closed circles) and AMP (open circles) concentrations in rat serum. METH was infused using a subcutaneous osmotic minipump and once steady state concentrations were reached, anti-METH mAb was administered. Rats were sacrificed at various time points for determination of serum METH and AMP concentrations. One way ANOVA followed by a Dunnett's test was used to compare control and post-mAb METH and AMP values. mAb6H4 significantly increased METH serum concentrations at the 1, 5, 30, 75, and 120 min, but not at 24 hr, compared to the pre-mAb levels. AMP concentrations were increased briefly at the 1 and 5 min time points. MAb4G9 significantly increased METH and AMP serum concentrations from 1 min to 24 hrs.

FIG. 8 depicts two graphs showing the effect of mAb6H4 (Panel A) and mAb4G9 (Panel B) on METH (closed circles) and AMP (open circles) concentrations in the rat brain. METH was infused using a subcutaneous osmotic minipump and once steady state concentrations were reached, anti-METH mAb was administered. Rats were sacrificed at various time points for determination of brain METH and AMP concentrations. One way ANOVA followed by a Dunnett's test was used to compare control and post-mAb METH and AMP values. METH brain levels significantly different from the no mAb group are indicated with *, while # indicates METH and AMP levels significantly different from the no mAb group. METH brain concentrations were decreased at all times except 24 hr after mAb6H4 treatment. mAb6H4 had no effect on AMP brain concentrations. mAb4G9 significantly decreased METH brain concentrations at all time points, while AMP brain concentrations were significantly decreased at the 5 and 30 min time points.

SUMMARY OF THE INVENTION

Figure 3:
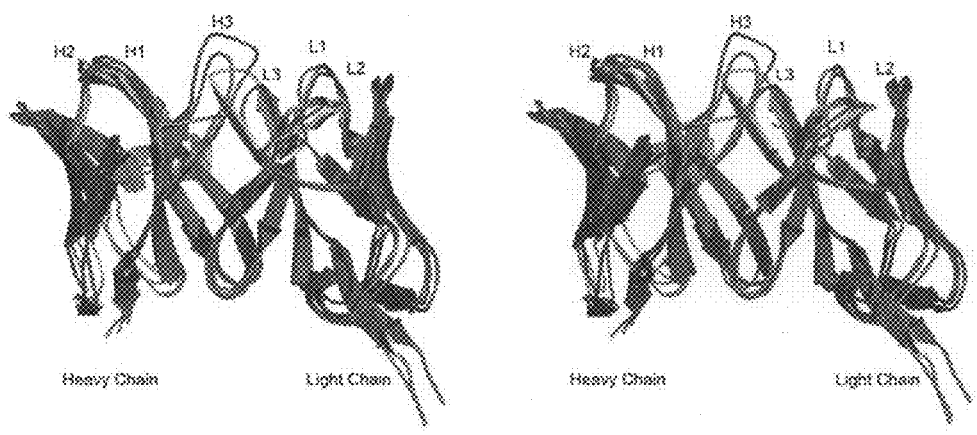
FIG. 3 presents molecular models of three anti-(+)METH mAb. Upper panel: Stereo view of superimposed molecular models of anti-(+)METH mAb. The variable regions of the three mAb were modeled, structurally aligned and represented in cartoon format. The framework residues are represented in blue. The CDRs are colored according to mAb: mAb6H4, blue; mAb6H8, red; mAb4G9, green. The heavy chain, light chain, and CDRs are labeled. Lower panel: Root mean square deviations (RMSD) (Å) of CDRs from the main chain conformation of mAb6H4.

One aspect of the invention encompasses a monoclonal antibody that recognizes each compound of the group consisting of (+)amphetamine, (+)methamphetamine, and (+)3,4-methylenedioxymethamphetamine.

Another aspect of the invention encompasses a monoclonal antibody that recognizes at least one compound of the group consisting of (+)amphetamine, (+)methamphetamine, and (+)3,4-methylenedioxymethamphetamine and does not substantially recognize (−)amphetamine, (−)methamphetamine, and (−)3,4-methylenedioxymethamphetamine. The antibody is generated using a compound of formula (I):

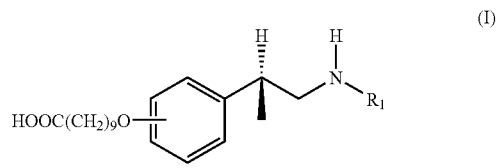

wherein:

$R_1$ is selected from the group consisting of hydrogen and methyl.

Yet another aspect of the invention encompasses a method of treating drug use in a subject. The method comprises administering to the subject a monoclonal antibody that recognizes each compound of the group consisting of (+)amphetamine, (+)methamphetamine, and (+)3,4-methylenedioxymethamphetamine. The monoclonal antibody decreases the concentration of at least one compound selected from the group consisting of (+)amphetamine, (+)methamphetamine, and (+)3,4-methylenedioxymethamphetamine in the brain of the subject.

Still another aspect of the invention encompasses a method of treating drug use in a subject. The method comprises administering to the subject a monoclonal antibody that recognizes at least one compound of the group consisting of (+)amphetamine, (+)methamphetamine, and (+)3,4-methylenedioxymethamphetamine and does not substantially recognize (−) amphetamine, (−)methamphetamine, and (−)3,4-methylenedioxymethamphetamine. The antibody is generated using a compound of formula (I):

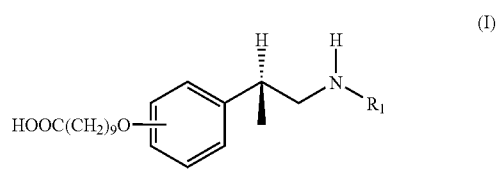

wherein:

$R_1$ is selected from the group consisting of hydrogen and methyl.

The monoclonal antibody decreases the concentration of (+)amphetamine, (+)methamphetamine, and (+)3,4-methylenedioxymethamphetamine in the brain of the subject.

A further aspect of the invention encompasses an assay for detecting the presence of at least one compound in a sample. The compound is selected from the group of compounds consisting of (+)methamphetamine, (+)amphetamine, and (+)3,4-methylenedioxymethamphetamine. The assay comprises contacting the sample with a monoclonal antibody that recognizes each compound of the group consisting of (+)amphetamine, (+)methamphetamine, and (+)3,4-methylenedioxymethamphetamine and detecting the association of the monoclonal antibody in the sample with at least one compound selected from the group consisting of (+)methamphetamine, (+)amphetamine, and (+)3,4-methylenedioxymethamphetamine.

Still a further aspect of the invention encompasses a kit. The kit comprises a monoclonal antibody that recognizes each compound of the group consisting of (+)amphetamine, (+)methamphetamine, and (+)3,4-methylenedioxymethamphetamine.

Other aspects and iterations of the invention are described more thoroughly below.

DETAILED DESCRIPTION OF THE INVENTION

The present invention provides monoclonal antibodies that have specificity and affinity for (+)methamphetamine and (+)methamphetamine-like compounds. These antibodies recognize at least one compound of the group consisting of (+)amphetamine, (+)methamphetamine, and (+)MDMA, and do not substantially recognize (−)amphetamine, (−)methamphetamine, and (−)MDMA. Because of their specificity and affinity, the monoclonal antibodies may be used to treat drug use in a subject.

I. Monoclonal Antibodies of the Invention

In one embodiment the monoclonal antibodies may recognize at least one compound of the group consisting of (+)methamphetamine, (+)amphetamine, and (+)MDMA. In another embodiment, the monoclonal antibodies may recognize at least two compounds from the group consisting of (+)methamphetamine, (+)amphetamine, and (+)MDMA. In an exemplary embodiment, the monoclonal antibodies may recognize all three compounds of the group consisting of (+)methamphetamine, (+)amphetamine, and (+)MDMA. In another exemplary embodiment, the monoclonal antibodies may recognize all three compounds of the group consisting of (+)methamphetamine, (+)amphetamine, and (+)MDMA, and not substantially recognize over the counter medications. In yet another exemplary embodiment, the monoclonal antibodies may recognize all three compounds of the group consisting of (+)methamphetamine, (+)amphetamine, and (+)MDMA, and not substantially recognize non-(+)methamphetamine like prescription medications. In each of the above embodiments, the monoclonal antibodies do not substantially recognize (−)methamphetamine, (−)amphetamine, and (−)MDMA.

An antibody of the invention "recognizes" a compound if the $IC_{50}$ ratio for that antibody is greater than about 20%. The $IC_{50}$ ratio may be calculated in reference to either (+)methamphetamine or (+)amphetamine. Typically, if the antibody is generated with a hapten derived from (+)methamphetamine, then the $IC_{50}$ ratio should be determined in reference to (+)methamphetamine. Similarly, if the antibody is generated with a hapten derived from (+)amphetamine, then the $IC_{50}$ ratio should be determined in reference to (+)amphetamine. For instance, if the hapten was derived from a compound of formula (I),

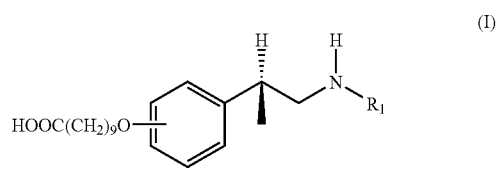

wherein $R_1$ is hydrogen (i.e. forming (+)amphetamine), then the $IC_{50}$ ratio should be determined in reference to (+)amphetamine. Alternatively, if $R_1$ of formula (I) is a methyl group (i.e. forming (+)methamphetamine), then the $IC_{50}$ ratio should be determined in reference to (+)methamphetamine.

In reference to (+)methamphetamine, the $IC_{50}$ ratio refers to the ratio of the $IC_{50}$ for (+)methamphetamine in the presence of labeled (+)methamphetamine to the $IC_{50}$ for a test ligand in the presence of labeled (+)methamphetamine. The $IC_{50}$ value is the concentration of test ligand required to inhibit 50% of the labeled (+)methamphetamine binding. For instance, see Table 2 in the Examples.

In reference to (+)amphetamine, the $IC_{50}$ ratio refers to the ratio of the $IC_{50}$ for (+)amphetamine in the presence of labeled (+)amphetamine to the $IC_{50}$ for a test ligand in the presence of labeled (+)amphetamine. The $IC_{50}$ value is the concentration of test ligand required to inhibit 50% of the labeled (+)amphetamine binding.

Irrespective of whether the $IC_{50}$ ratio is determined in reference to (+)methamphetamine or (+)amphetamine, an antibody of the invention "recognizes" a compound if the $IC_{50}$ ratio is greater than about 20%. In one embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine (e.g. an anti-(+) METH monoclonal antibody).

In another embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)amphetamine (e.g. an anti-(+)AMP monoclonal antibody).

In yet another embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)MDMA (e.g. an anti-(+)MDMA monoclonal antibody).

In still another embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine and (+)amphetamine (e.g. an anti-(+)METH/(+)AMP monoclonal antibody).

In a further embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine and (+)MDMA (e.g. an anti-(+)METH/(+)MDMA monoclonal antibody).

In a further embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)amphetamine and (+)MDMA (e.g. an anti-(+)AMP/(+)MDMA monoclonal antibody).

In an exemplary embodiment, a monoclonal antibody of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine, (+)amphetamine, and (+)MDMA (e.g. an anti-(+)METH/(+)AMP/(+)MDMA monoclonal antibody).

An antibody of the invention "substantially does not recognize" a compound if the $IC_{50}$ ratio is less than about 15%. In one embodiment, a monoclonal antibody of the invention has an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for (−)methamphetamine, (−)amphetamine, and (−)MDMA. In another embodiment, a monoclonal antibody of the invention may have an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for over the counter medications. In yet another embodiment, a monoclonal antibody of the invention may have an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for non-(+)methamphetamine like prescription medications.

The invention also encompasses the amino acid and nucleic acid sequences of monoclonal antibodies of the invention. For instance, in one embodiment, the heavy chain of a monoclonal antibody of the invention has the amino acid sequence of SEQ ID NO:25 or SEQ ID NO:19. In another embodiment, heavy chain of a monoclonal antibody of the invention has the nucleic acid sequence of SEQ ID NO:23 or SEQ ID NO:20. In yet another embodiment, the light chain of a monoclonal antibody of the invention has the amino acid sequence of SEQ ID NO:26 or SEQ ID NO:21. In still another embodiment, the light chain of a monoclonal antibody of the invention has the nucleic acid sequence of SEQ ID NO:24 or SEQ ID NO:22.

An exemplary embodiment of a monoclonal antibody that recognizes each compound of the group consisting of (+)methamphetamine, (+)amphetamine, and (+)MDMA, but does not substantially recognize (−)methamphetamine, (−)amphetamine, and (−)MDMA is a monoclonal antibody comprising the heavy chain amino acid sequence of SEQ ID NO:25 and the light chain amino acid sequence of SEQ ID NO:26 [i.e. the monoclonal antibody referred to herein as mAb4G9]. Another exemplary embodiment of an antibody that recognizes each compound of the group consisting of (+)methamphetamine, (+)amphetamine, and (+)MDMA, but does not substantially recognize (−)methamphetamine, (−)amphetamine, and (−)MDMA is a monoclonal antibody comprising the heavy chain amino acid sequence of SEQ ID NO:19 and the light chain amino acid sequence of SEQ ID NO:21 [i.e. the monoclonal antibody referred to herein as mAb2F11].

The monoclonal antibodies may be murine monoclonal antibodies, human monoclonal antibodies, humanized monoclonal antibodies, chimeric monoclonal antibodies, recombinant monoclonal antibodies, or monoclonal antibody fragments without departing from the scope of the invention. In one embodiment, the invention encompasses murine monoclonal antibodies. Non-limiting examples of murine monoclonal antibodies include mouse and rat monoclonal antibodies. In another embodiment, the invention encompasses human monoclonal antibodies. In yet another embodiment, the invention encompasses humanized monoclonal antibodies. In still yet another embodiment, the invention encompasses chimeric monoclonal antibodies. In an alternative embodiment, the invention encompasses recombinant monoclonal antibodies. Recombinant monoclonal antibodies include antibodies that have been engineered so as to reduce the antibodies' immunogenicity when used as a medication. In another alternative, the invention encompasses monoclonal antibody fragments. Non-limiting examples of such fragments include Fab fragments, Fab' fragments, F(ab')$_2$ fragments, single chain antigen binding fragments (scFv), disulfide stabilized Fv (dsFv) fragments, single domain antigen binding fragments, and other antibody fragments that maintain the binding specificity of the whole monoclonal antibody but that are less immunogenic, more cost-effective to produce, or more pharmaceutically effective than the whole monoclonal antibody.

Monoclonal antibodies may have lambda, kappa, or a recombinant light chain. Additionally, monoclonal antibodies are typically, but not necessarily, IgG antibodies. In certain embodiments, the IgG antibodies may include antibodies from the IgG1, IgG2, IgG3, and IgG4 human antibody classes. In other embodiments, the IgG antibodies may include antibodies from the IgG1, IgG2a, IgG2b, and IgG3 mouse antibody classes.

II. Methods of Making Monoclonal Antibodies a. Hapten Compounds for Making Monoclonal Antibodies Hapten compounds may be used to elicit monoclonal antibodies that recognize at least one of the compounds selected from the group consisting of (+)methamphetamine, (+)amphetamine, and (+)MDMA, but not substantially recognize (−)methamphetamine, (−)amphetamine, and (−)MDMA. In certain embodiments, the hapten compound is designed to generate monoclonal antibodies that recognize at least two compounds from the group consisting of (+)methamphetamine, (+)amphetamine, and (+)MDMA. In an exemplary embodiment, the hapten compound is designed to generate monoclonal antibodies that recognize all three compounds of the group consisting of (+)methamphetamine, (+)amphetamine, and (+)MDMA. Typically, such a hapten compound will comprise either (+)methamphetamine or (+)amphetamine conjugated to a linker (L).

In general, L is comprised of atoms and is of a sufficient length so that L is flexible enough to facilitate an orientation of the (+)methamphetamine or (+) amphetamine sufficient to generate desired antibodies. In this context, "desired" antibodies include antibodies that recognize at least one compound selected from the group consisting of (+)methamphetamine, (+)amphetamine, and (+)MDMA. L is also typically not strongly immunogenic. In other words, L may be designed so that antibodies generated against a compound of the invention recognize the compound without the need for L to be linked to the compound or present in a subject during treatment.

The exact length of L can and will vary. Typically, L is at least 9 angstroms long. In one embodiment, L may be from about 9 angstroms to about 27 or more angstroms long. In another embodiment, L is at least 11 angstroms, at least 12 angstroms, at least 13 angstroms, at least 14 angstroms, at least 15 angstroms, at least 16 angstroms, at least 17 angstroms, at least 18 angstroms, at least 19 angstroms, at least 20 angstroms, at least 21 angstroms, at least 22 angstroms, at least 23 angstroms, at least 24 angstroms, at least 25 angstroms, at least 26 angstroms, or at least 27 angstroms. The length of the linker when expressed in angstroms may be determined by performing a modeling study, using, for instance, the MM94 force field. Stated another way, the length of L may be expressed as the number of contiguous atoms forming the shortest path from one substructure that L connects to the other substructure. In one embodiment, L is at least 6 contiguous atoms in length. In another embodiment, L may be from about 8 to about 100 or more atoms in length. In an additional embodiment, L is 6, 7, 8, 9, 10, 11, 12, 13, 14, 15, 16, 17, 18, 19, 20, 21, 22, 23, 24, 25, 26, 27, 28, 29, or 30 or more contiguous atoms in length.

As will be appreciated by a skilled artisan, the atoms comprising L may vary widely. Typically, the atoms impart the appropriate degree of flexibility, as detailed above. Suitable atoms forming L may be selected from the group comprising hydrocarbyl, substituted hydrocarbyls, and heteroatoms. In some embodiments, L may be comprised of amino acids, such as glycine or proline. For instance, L may be a peptide. In other embodiments, L may be comprised of nucleotides. In further embodiments, L may be linear, branched, or may comprise ring structures.

It is also envisioned that L may be attached to the benzene ring of (+)methamphetamine or (+)amphetamine at a variety of positions without departing from the scope of the invention. For example, in one embodiment, L may be attached at the meta position of the benzene ring. In another embodiment, L may be attached at the ortho position. In yet another embodiment, L may be attached at the para position.

In an exemplary embodiment, the hapten compound may comprise a compound of formula (I):

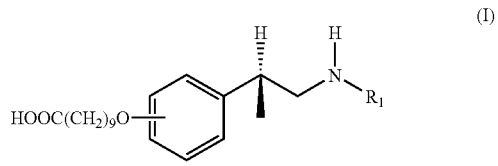

wherein:

$R_1$ is selected from the group consisting of hydrogen and methyl.

In some embodiments, $R_1$ is hydrogen (i.e., forming (+) amphetamine). In other embodiments, $R_1$ is a methyl group (i.e., forming (+) methamphetamine). In formula (I), L is represented by the —O(CH$_2$)$_9$COOH group. Therefore, in one embodiment, the —O(CH$_2$)$_9$COOH group may be in the ortho position. In another embodiment, the —O(CH$_2$)$_9$COOH group may be in the meta position. In yet another embodiment, the —O(CH$_2$)$_9$COOH group may be in the para position. In other exemplary embodiments, the hapten compound may comprise a compound listed in Table 1 or Example 1 herein.

b. Immunizing Agents Comprising Hapten Compounds

To elicit an antibody response, immunizing agents comprising hapten compounds may be used. In certain embodiments, an immunizing agent may comprise a hapten compound and an adjuvant. Generally speaking, an adjuvant may be used to increase the immune response to a hapten compound. For instance, an adjuvant may be used to increase antibody affinity, antibody titer, and the duration of the immune response. Non-limiting examples of adjuvants include alum, TiterMax Gold, Ribi, ASO4, Freund's complete adjuvant, and Freund's incomplete adjuvant. In one embodiment, the adjuvant may be alum. In another embodiment, the adjuvant may be TiterMax Gold. In yet another embodiment, the adjuvant may be Ribi. In still another embodiment, the adjuvant may be ASO4. In still yet another embodiment, the adjuvant may be Freund's complete adjuvant. In an additional embodiment, the adjuvant may be Freund's incomplete adjuvant.

In some embodiments, an immunizing agent may further comprise a pharmaceutically acceptable carrier. Briefly, a pharmaceutically acceptable carrier safely elicits an antibody response in a subject. In this context, safely means that the carrier does not substantially elicit an immune response that cross-reacts with a self-protein, or a regularly ingested protein. Typically, the carrier may be a protein, lipid, carbohydrate, or any combination thereof that is capable of eliciting an immune response. In some embodiments, the carrier is a protein. In a particular embodiment, the carrier may be selected from the group of proteins comprising keyhole limpet hemocyanin (KLH), ovalbumin, bovine serum albumin (BSA), sheep albumin, thyroglobulin, and any modifications, derivatives, or analogues thereof. For instance, in one embodiment, the carrier may be BSA or cationized BSA. In another embodiment, the carrier may be KLH. In yet another embodiment, the carrier may be thyroglobulin.

In another particular embodiment, the carrier may be a bacterial toxin or toxoid. Non-limiting examples of suitable bacterial toxins or toxoids may include tetanus toxoid, diphtheria toxoid, non-toxic mutant diphtheria toxoid $CRM_{197}$, outer membrane protein complex (OMPC) from Neisseria meningitidis, the B subunit of heat-labile *Escherichia coli*, recombinant exoprotein A from *Pseudomonas aeruginosa* (rEPA), cholera toxin B-(CTB), pertussis toxin and filamentous hemagglutinin, shiga toxin, and the LTB family of bacterial toxins.

In an alternative embodiment, an immunizing agent comprising a hapten compound may further comprise an excipient. Non-limiting examples of excipients include sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose, and buffer. Other suitable excipients may be used by those skilled in that art.

c. Hybridoma Methods

Monoclonal antibodies may be prepared using hybridoma methods, such as those described by Kohler and Milstein, Nature, 256:495 (1975). In a hybridoma method, a mouse, hamster, or other appropriate host animal is typically immunized with an immunizing agent, as described above, to elicit lymphocytes that produce or are capable of producing antibodies that will specifically bind to the immunizing agent. Alternatively, the lymphocytes may be immunized in vitro.

The immunizing agent will typically comprise a hapten compound capable of eliciting antibodies that recognize at least one of the compounds selected from the group consisting of (+)methamphetamine, (+)amphetamine, and (+)MDMA, but not substantially recognize (−)methamphetamine, (−)amphetamine, and (−)MDMA, as described above and as detailed in the examples.

Generally, the lymphocytes from the host animal immunized with a hapten compound are collected and fused with an immortalized cell line using a suitable fusing agent, such as polyethylene glycol, to form a hybridoma cell [Goding, Monoclonal Antibodies: Principles and Practice, Academic Press, (1986) pp. 59 103]. Peripheral blood lymphocytes ("PBLs") may be used if cells of human origin are desired, or spleen cells or lymph node cells may be used if non-human mammalian sources are desired. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51 63].

The culture medium in which the hybridoma cells are cultured can then be assayed for the presence of monoclonal antibodies that recognize at least one compound selected from the group consisting of (+)methamphetamine, (+)amphetamine, and (+)MDMA, but do not substantially recognize (−)methamphetamine, (−)amphetamine, and (−)MDMA. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). In an exemplary embodiment, the binding specificity is determined using the RIA method detailed in the Examples.

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G-Sepharose, hydroxyapatite chromatography, ion exchange chromatography, gel electrophoresis, dialysis, or affinity chromatography.

d. Recombinant Antibody Methods

The monoclonal antibodies may also be made by recombinant DNA methods, such as those described in U.S. Pat. No.

4,816,567. DNA (including cDNA derived from reverse transcription of RNA) encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric antibody. Methods of creating recombinant or chimeric antibodies are well known in the art. See, for instance, Harlow and Lane, Antibodies: a Laboratory Manual, Cold Spring Harbor Laboratory (1988).

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Monoclonal antibodies and antibody fragments may also be produced in plant expression systems. For more details, see Peterson et al., The AAPS Journal 2006; 8(2): E383.

e. Human and Humanized Antibody Methods

The monoclonal antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region, typically that of a human immunoglobulin [Jones et al., Nature, 321:522 525 (1986); Riechmann et al., Nature, 332:323 329 (1988); and Presta, Curr. Op. Struct. Biol., 2:593 596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522 525 (1986); Riechmann et al., Nature, 332:323 327 (1988); Verhoeyen et al., Science, 239:1534 1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86 95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al, Nature Biotechnology 14:845-51 (1996); Neuberger, Nature Biotechnology 14:826 (1996); Lonberg and Huszar, Intern. Rev. Immunol. 13:65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

III. Methods of Using the Monoclonal Antibodies

A further aspect of the invention encompasses both therapeutic and non-therapeutic uses for the monoclonal antibodies generated using the methods of section II above.

a. Non-Therapeutic Uses

In certain embodiments, the monoclonal antibodies may be used in non-therapeutic assays, such as immunostaining, immunoprecipitation, immunoblotting, immunoaffinity purification, immunochromatographic assays, lateral-flow assays and ELISAs. In one embodiment, the monoclonal antibodies may be used for immunostaining. In another embodiment, the monoclonal antibodies may be used for immunoprecipitation. In yet another embodiment, the monoclonal antibodies may be used for immunoblotting. In still another embodiment, the monoclonal antibodies may be used for immunoaffinity purification. In still yet another embodiment, the monoclonal antibodies may be used for ELISAs. In an alternative embodiment, the monoclonal antibodies may be used for immunochromatographic assays. In another alternative embodiment, the monoclonal antibodies may be used for lateral-flow assays. Protocols for each of the above non-therapeutic uses are well known in the art, and may be found, for instance, in Harlow and Lane, *Antibodies*, Cold Spring Harbor, 1988, Chapters 9-14, U.S. Pat. Nos. 5,160,701, 5,141,850, 5,451,504, 5,415,994, and 5,559,041, hereby incorporated by reference.

Additionally, one or more monoclonal antibodies of the invention may be used for detecting (+)methamphetamine, (+)amphetamine, and (+)MDMA in a sample using a non-therapeutic assay described above. For example, one embodiment of the invention is an assay for detecting the presence of at least one compound in a sample selected from the group of compounds consisting of (+)methamphetamine, (+)amphetamine, and (+)3,4-methylenedioxymethamphetamine. The assay comprises contacting the sample with a monoclonal antibody of the invention and detecting the association of the monoclonal antibody in the sample with at least one compound selected from the group consisting of (+)methamphetamine, (+)amphetamine, and (+)3,4-methylenedioxymethamphetamine. In some embodiments, the assay may further comprise quantifying the amount of a compound in the sample selected from the group of compounds consisting of (+)methamphetamine, (+)amphetamine, and (+)3,4-methylenedioxymethamphetamine.

A monoclonal antibody may be used to detect and/or quantify at least one compound from the group consisting of (+)methamphetamine, (+)amphetamine, and (+)MDMA in a sample. In another embodiment, a monoclonal antibody may be used to detect and/or quantify at least two compounds from the group consisting of (+)methamphetamine, (+)amphetamine, and (+)MDMA in a sample. In yet another embodiment a monoclonal antibody may be used to detect and/or quantify each compound of the group consisting of (+)methamphetamine, (+)amphetamine, and (+)MDMA in a sample. In an alternative embodiment, more than one monoclonal antibody may be used to detect and/or quantify each compound of the group consisting of (+)methamphetamine, (+)amphetamine, and (+)MDMA in a sample. Methods and devices for using antibodies to detect and/or quantify substances in samples are well known in the art. For instance, see U.S. Pat. No. 5,328,828.

As used herein, "sample" may refer to a biological sample from a subject or a sample of a chemical substance. Non-limiting examples of biological samples from a subject may include fluid samples or tissue samples. Fluid samples may include blood (including serum or plasma), urine, saliva, or other biological fluids that could comprise (+)methamphetamine, (+)amphetamine, or (+)MDMA. Tissue samples may include hair or skin samples, or other biological tissues that could comprise (+)methamphetamine, (+)amphetamine, or (+)MDMA. Methods of collecting biological samples are well known in the art. Non-limiting examples of chemical substances may include powders, pills, and liquids. For instance, a monoclonal antibody of the invention may be used to detect (+)methamphetamine, (+)amphetamine, or (+)MDMA in a powder of unknown composition.

b. Therapeutic Uses

Additionally, the monoclonal antibodies may be used for therapeutic purposes. Generally speaking, the monoclonal antibodies may be used to antagonize the effects of (+)methamphetamine, (+)amphetamine, and/or (+)MDMA in a subject. In certain embodiments, the subjects may be using (+)methamphetamine, (+)amphetamine, and/or (+)MDMA. For instance, in one embodiment, the monoclonal antibodies may antagonize the effects of (+)methamphetamine, (+)amphetamine, and/or (+)MDMA in a subject by decreasing the concentration of (+)methamphetamine, (+)amphetamine, or (+)MDMA in the brain of a subject. In another embodiment, the monoclonal antibodies may be used to decrease drug-seeking behavior in a subject. In yet another embodiment, the monoclonal antibodies may be used to decrease self-dosing behavior in a subject. Methods for each of the above embodiments may be found in the examples.

In each of the above embodiments, the monoclonal antibodies may be administered passively. Passive administration typically refers to administering at least one monoclonal antibody, generated by a subject, to a second subject, or alternatively, administering at least one monoclonal antibody produced via ex vivo methods to a subject.

In one embodiment, the invention may encompass a method of treating drug use. The method may comprise administering a monoclonal antibody to a subject, wherein the passive administration decreases the concentration of (+)methamphetamine, (+)amphetamine, or (+)MDMA in the brain of the subject. In another embodiment, the method may comprise administering a monoclonal antibody to a subject, wherein the monoclonal antibody decreases the concentration of two or more of the group consisting of (+)methamphetamine, (+)amphetamine, or (+)MDMA in the brain of the subject In yet another embodiment, the method may comprise administering a monoclonal antibody to a subject, wherein the monoclonal antibody decreases the concentration of (+)amphetamine, (+)methamphetamine, and (+)3,4-methylenedioxymethamphetamine in the brain of the subject.

Alternatively, the method of treating drug use may comprise administering more than one monoclonal antibody to a subject to decrease the concentration of (+)methamphetamine, (+)amphetamine, or (+)MDMA in the brain of the subject. If more than one antibody is administered to a subject, the antibodies may be administered simultaneously or sequentially. In one embodiment, each monoclonal antibody administered to a subject has a different pharmacokinetic profile. For instance, a monoclonal antibody that has a short half-life may be administered together with a monoclonal antibody that has a longer half-life. In another embodiment, each monoclonal antibody administered to a subject has a different affinity for a particular target compound. For instance, a monoclonal antibody that recognizes (+)methamphetamine may be administered together with a monoclonal antibody that recognizes (+)amphetamine. Alternatively, a monoclonal antibody that recognizes at least one compound selected from the group comprising (+)methamphetamine, (+)amphetamine, and (+)MDMA may be administered with a monoclonal antibody that recognizes another drug of abuse, such as cocaine, phencyclidine, opioids, or nicotine.

c. Pharmaceutical Compositions

The monoclonal antibodies of the present invention can be formulated into pharmaceutical compositions and administered by a number of different means that will deliver a therapeutically effective dose. Such compositions may be administered orally, parenterally, by inhalation spray, rectally, intradermally, or transdermally, in dosage unit formulations containing conventional nontoxic pharmaceutically acceptable carriers, adjuvants, and vehicles as desired. The term parenteral as used herein includes subcutaneous, intravenous, intramuscular, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and nonionic detergents, and polyethylene glycols can be used. Mixtures of solvents and wetting agents such as those discussed above are also useful.

For therapeutic purposes, formulations for parenteral administration may be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of the compound of the invention that can be combined with the carrier materials to produce a single dosage of the composition will vary depending upon the patient and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493. Generally speaking, the dosage of monoclonal antibody may be from about 1 ng/kg subject body weight per month to about 1 g/kg subject body weight per month. In one embodiment, the dosage of monoclonal antibody may be from about 1 mg/kg subject body weight per month to about 125 mg/kg subject body weight per month. In another embodiment, the dosage of monoclonal antibody may be from about 10 mg/kg subject body weight per month to about 150 mg/kg subject body weight per month. In yet another embodiment, the dosage of monoclonal antibody may be from about 25 mg/kg subject body weight per month to about 100 mg/kg subject body weight per month. In a preferred embodiment, the dosage of monoclonal antibody may be from about 25 mg/kg subject body weight per month to about 40 mg/kg subject body weight per month.

d. Kits

A further aspect of the invention encompasses kits. The kits typically comprise an antibody of the invention described above. The kits may further comprise instructions for detecting and/or quantifying the presence of at least one compound in a sample selected from the group of compounds consisting of (+)methamphetamine, (+)amphetamine, and (+)3,4-methylenedioxymethamphetamine using the methods described above and in the Examples. The kits may also comprise means for collecting a sample. In some embodiments, the sample may be biological. In other embodiments, the sample may be chemical. For instance, in certain embodiments the kits may be used for detecting and/or quantifying the presence of at least one compound in a hair or blood sample selected from the group of compounds consisting of (+)methamphetamine, (+)amphetamine, and (+)3,4-methylenedioxymethamphetamine.

DEFINITIONS

As used herein "(d)" stands for dextrorotatory and "(l)" stands for levorotatory, and refers to the direction in which an enantiomer rotates the plane of polarized light. Herein, (d) is used interchangeably with (+), and (l) is used interchangeably with (−).

Unless otherwise indicated, the alkyl groups described herein are preferably lower alkyl containing from one to eight carbon atoms in the principal chain and up to 30 carbon atoms or more. They may be straight or branched chain or cyclic and include methyl, ethyl, propyl, isopropyl, butyl, hexyl and the like. Unless otherwise indicated, the alkenyl groups described herein are preferably lower alkenyl containing from two to eight carbon atoms in the principal chain and up to 30 carbon atoms or more. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 30 carbon atoms or more. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The phrase "decreasing the concentration of (+)methamphetamine, (+)amphetamine, or (+)MDMA in the brain" may refer to either decreasing the amount of (+)methamphetamine, (+)amphetamine, or (+)MDMA in the brain, or changing the rate of entry of (+)methamphetamine, (+)amphetamine, or (+)MDMA into the brain.

The term "hapten" refers to a partial or incomplete antigen. Haptens are protein-free substances that generally are not capable of stimulating antibody formation, but may react with antibodies. Amphetamine, methamphetamine, and their derivatives are haptens.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring.

The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo groups include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl.

The term "subject" as used herein refers to a mammal. Suitable mammals may include mice, rats, dogs, non-human primates, and humans.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents may include one or more of the following groups: halogen, carbocycle, carboxy, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the invention.

Example 1

Hapten Design and Antibody Selection

When generating monoclonal antibodies (mAb, plural and singular) against small molecules, the chemical composition and molecular orientation of the drug-like hapten on the antigen is a crucial determinant. This is especially important when attempting to discover therapeutic mAb against the drugs of abuse (+)methamphetamine ((+)METH), (+)amphetamine ((+)AMP) and the related compound (+)3,4-methylenedioxymethamphetamine ((+)MDMA, the plus isomer in the racemic mixture known as MDMA or ecstasy). The goal of these studies was to design and synthesize (+)METH-like haptens with structural attributes that would make them effective for generating monoclonal antibodies for treating medical problems associated with these stimulant drugs of abuse.

For these studies, hapten spacers between (+)METH and the carrier protein were progressively lengthened from 4 to 10 atoms to increase the potential for greater interaction of the hapten with the antibody binding site and/or to increase flexibility of the spacer between the (+)METH backbone structure and the carrier. It was hypothesized that a progressive lengthening and flexibility of the spacer arm would lead to increased affinity and specificity due to increased access to the entire (+)METH-like structure. As a secondary strategy, the location of the linker attachment to the (+)METH structure (e.g., para and meta attachments) was varied in an attempt to elicit antibodies with different conformational selectivity for (+)METH-like compounds.

Chemicals and Drugs. All chemicals and protein antigens were purchased from Sigma (St. Louis, Mo.), unless otherwise noted. Enzymes and *E. coli* strains were purchased from Invitrogen (Carlsbad, Calif.). (+)-[2',6'-$^3$H(n)]-methamphetamine ([$^3$H]-(+)METH; 23.5 Ci/mmol) and (±)-[2,6-$^3$H(n)]-amphetamine ([$^3$H]-(±)AMP; 45 Ci/mmol) were obtained from the National Institute on Drug Abuse (Bethesda, Md.) after synthesis at the Research Triangle Institute (Research Triangle Park, N.C.). Other METH-like drugs used in this study were also obtained from the National Institute on Drug Abuse.

[$^3$H]-(+)METH was used as sent, but the [$^3$H]-(±)AMP was chromatographically separated to obtain [$^3$H]-(+)AMP for use in our studies of (+)AMP specificity. The separation was performed on a 150×4 mm (i.d.) 5 μm CrownPak CR(+) column (Chiral Technologies Inc., Exton, Pa.). The mobile phase consisted of 0.1 M perchloric acid (Fisher Scientific) containing 10% (v/v) methanol. The column temperature was maintained at 15° C. The flow rate was 1.0 ml/min and the injection volume was 50 μL. Chromatographic peaks were detected using ultraviolet absorption detection at a wavelength of 210 nm. The retention times for [$^3$H]-(+)AMP and [$^3$H]-(−)AMP were 20.1 min and 24.4 min, respectively.

Haptens and hapten-protein conjugation. Five different stereospecific (+)-isomer (+)METH-like haptens were synthesized. All haptens were synthesized as HCl salts to aid in solubility, and stored as solids or powders until used. The chemical structures are shown in Table 1. The complete synthesis of one of the haptens ((+)METH P6) was previously reported (Byrnes-Blake et al., 2001, Int Immunopharmacol 1:329-338). The chemical names and abbreviations of the five haptens are:

(S)-(+)-4-(3-carboxypropyl)methamphetamine, (+)METH P4

(S)-(+)-4-(5-carboxypentyl)methamphetamine, (+)METH P6

(S)-(+)-4-(5-carboxypentyloxy)methamphetamine, (+)METH P06

(S)-(+)-3-(5-carboxypentyloxy)methamphetamine, (+)METH M06

(S)-(+)-3-(9-carboxynonyloxy)methamphetamine, (+)METH M010

Each hapten was initially covalently bound to at least 2-3 different protein antigens and used for immunization of mice to test for anti-METH IgG response. The individual mouse and hapten-protein antigen combination that yielded the highest anti-(+)METH IgG titers was chosen for production of monoclonal antibodies (see details below). The following is a list of the hapten-protein conjugates that produced the mAb listed in Table 1: (+)METH P4 and (+)METH P6 conjugated to bovine serum albumin; (+)METH PO6 and (+)METH MO6 conjugated to Inject Supercarrier Immune Modulator (cationized BSA (cBSA), Pierce Biotech, Rockford, Ill.); (+)METH MO10 conjugated to ovalbumin (OVA).

All chemical reactions for covalent binding of the haptens to protein antigens followed the same general procedure. The haptens were first solubilized in either 0.1 M 2-[N-morpholino]ethanesulfonic acid buffer (pH 4.5) or dimethylformamide and then adjusted to pH 4.5 with HCl. All haptens were coupled to their respective protein antigens by a carbodiimide reaction using the cross-linker 1-ethyl-3-[3-dimethylaminopropyl]carbodiimide hydrochloride (Pierce Biotech). This chemical synthesis forms a peptide bond between the carboxyl group of the hapten linker arm and free amino groups of lysine side chains in the respective proteins. The reactions were conducted with continuous stirring under dark conditions at room temperature for 18 hrs. At the end of the reaction, all antigens were purified as described by Byrnes-Blake et al. (2003, Eur J Pharmacol 461:119-128). This purification involved dialysis against distilled water, phosphate-buffered saline (pH 7.4), and a final purification of the soluble fraction on a gel filtration column in phosphate-buffered saline (pH 7.4). Purified antigens were stored at −20° C. until needed.

Immunization, screening, and hybridoma generation. Female BALB/c mice (Charles River Laboratories, Wilmington, Mass.) were used for all immunizations. For production of the (+)METH P6 mAb, mice were immunized subcutaneously in the hindquarters with 100 µg of the (+)METH P6 antigen emulsified 1:1 (v/v) in TiterMax adjuvant (CytRx Corporation, Norcross, Ga.) and boosted monthly with 50 µg of the antigen until a favorable titer was reached. For all other antigen immunizations, the mice were initially immunized in the hindquarters subcutaneously with 20-100 µg of antigen emulsified in Freund's complete adjuvant. The initial immunization was followed by a boost with 20-50 µg of antigen emulsified in Freund's incomplete adjuvant three weeks later followed by three boosts at six week intervals, until a favorable titer level was reached. Serum samples were taken via tail bleed periodically to measure anti-(+)METH IgG. Titers were measured by ELISA (enzyme-linked immunosorbant assay) using 96-well microtiter plates coated with the original hapten conjugated to a different protein. For example, if the original antigen was (+)METH-MO6-cBSA, (+)METH-MO6 conjugated to thyroglobulin was used to avoid selecting carrier protein-reactive antibodies. The screening for anti-(+) METH IgG response was conducted by ELISA or a [$^3$H]-(+) METH radioimmunoassay (RIA), using (+)METH and (+)AMP as the inhibitors. After sufficient anti-(+)METH IgG titers were achieved, conventional hybridoma technology was utilized as described previously (Valentine et al, 1994, J Pharmacol Exp Ther 269:1079-1085). The hybridoma fusion partner for mouse B cells was cell line P3X63Ag8.653 (American Type Culture Collection, Manassas, Va.). IgG isotype and light chain identity was determined with a mouse antibody isotyping kit (Boehringer Mannheim, Indianapolis, Ind.).

Production and purification. Monoclonal antibodies were produced in either a Cell-Pharm System 2500 hollow fiber bioreactor (Valentine et al, 1996, J Pharmacol Exp Ther 278: 709-716; Unisyn Technologies, Inc., Hopkinton, Mass.) or in a Biostat B10 liter bioreactor (Sartorius Corp, Edgewood, N.Y.). All antibodies were harvested and stored at −80° C. until purification. mAb were purified either by affinity chromatography using Protein-G Sepharose (Amersham Biosciences, Piscataway, N.J.), or ion exchange chromatography using SP Sepharose (Amersham Biosciences, Piscataway, N.J.) as described in Hardin et al. (1998, J Pharmacol Exp Ther 285:1113-1122), or a combination of the two methods. Following purification, all antibodies were concentrated and buffer exchanged into 15 mM sodium phosphate containing 150 mM sodium chloride (pH 6.5-7.5) as described in McMillan et al. (2002, Behav Pharmacol 13:465-473).

Determination of immunochemical specificity. The cross-reactivity profiles of each mAb for methamphetamine, and structurally related and unrelated compounds, were determined by RIA in a manner similar to that described by Owens et al. (1988, J Pharmacol Exp Ther 246:472-478). An $IC_{50}$ value for inhibition of [$^3$H]-(+)METH binding (and [$^3$H]-(+) AMP for the mAb generated against the (+)METH MO10 hapten) was determined for each ligand after fitting a sigmoidal curve to the data points. $K_D$ values for mAb were determined by the method of Akera and Cheng (1977, Biochim Biophys Acta 470:412-423).

Results. For these studies, the hapten linkers were progressively lengthened from 4-10 atoms to increase the potential for greater interaction of the METH-like structures with the antibody binding site and to increase the flexibility of the spacer. It was hypothesized that a progressive lengthening of the spacer arm would lead to increases in affinity due to improved access to the entire METH-like structure; and the different immobilized conformations would elicit antibodies having different conformational selectivity for (+)METH-like compounds.

The haptens were conjugated to the terminal amino groups of lysines on all carrier proteins by carbodiimide chemistry, which forms a peptide bond with the available carboxylic acid on the hapten. There were 59 lysines in bovine serum albumin, 20 in each of the four subunits of ovalbumin and even more conjugation sites were available on cationized bovine serum albumin (i.e., Imject Supercarrier Immune Modulator). However not all of the lysines or conjugation sites were available at the surface of the protein for coupling to the haptens. Preliminary optimization experiments showed that a ratio of hapten to protein of 30:1 to 90:1 yielded the best incorporation rates for the syntheses. While the hapten incorporation rate for the antigens could not be precisely determined, initial mass spectrophotometry studies indicated that an average of 4 haptens were conjugated to each molecule of protein (data not shown).

Because the primary goal was to select for high-affinity mAb, the antigen dose was kept relatively low (e.g., 10-20 µg). While immunization with higher hapten-antigen doses (e.g., 50-100 µg) sometimes led to higher titers, the affinity for (+)METH was often too low. Thus a minimum dose of antigen was typically used. This strategy routinely led to immunological response in only 40-70% of animals. In more recent studies, it was discovered that a primary reason for <100% immunological response was the low incorporation rate of the hapten on protein antigens, which in part was overcome by judicious use of Freund's complete and incomplete adjuvants to boost and sustain immunological response.

Each mouse serum from each group of immunizations was routinely screened (typically 6-10 mice) after each boost to determine the maturity of the immune response and the relative immunochemical characteristics of the polyclonal serum (titer, affinity and specificity). For this, a [$^3$H]-(+)METH RIA was used. The screening assay always involved inhibitions of

[³H](+)METH binding with increasing doses of (+)METH and (+)AMP to determine the relative affinities for each ligand. The final choice of a specific mouse for use in generating hybridomas was based primarily on the animal with the highest titer and affinity for (+)METH. From this process of screening immune serum, 3-10 unique monoclonal antibodies were generally found from each fusion. Most importantly, a polyclonal antiserum that was positive for (+)AMP was not discovered until the MO10 hapten was used.

For producing the hybridomas, mice were chosen that had been immunized with Freund's complete adjuvant and boosted with Freund's incomplete adjuvant. The one exception was the immunizations with (+)METH P6, which used Titermax as the adjuvant. In preliminary optimization experiments, immunizations with alum precipitated antigens, Titermax adjuvant and Ribi's adjuvant were tried on several occasions. While these adjuvants generally produced high titers, it was found that the highest affinity antibodies were generated with Freund's adjuvants.

nochemical characteristics were extensively studied for molecular properties and preclinical efficacy (see Table 1). The rest of the hybridoma cell lines were stored frozen in case of future need. The selection of a mAb for more extensive in vitro and in vivo testing was based on the desire to have a range of affinities, a range of drug specificities, and a high level of mAb production from the parent hybridoma cell line. This final criterion was needed to increase the feasibility of large scale mAb production for in vivo testing. In most cases there was one or more similar affinity or specificity mAb that were produced from the same fusion. For instance, the separate fusions that produced mAb6H4 and mAb4G9 (see Table 1) also produced mAb with virtually the same affinity and specificity, but slightly different amino acid sequences. These two particular antibodies were chosen because the parent hybridoma cell line produced significantly more mAb.

TABLE 1

Chemical Structure of Haptens, the Resulting mAb, and $K_D$ Values for Key Drugs

| Hapten Structure | Hapten Name | mAb Name (Isotype and light chain) | (+)METH $K_D$ (nM) | (+)AMP $K_D$ (nM) | (+)MDMA $K_D$ (nM) |
|---|---|---|---|---|---|
| | (+)METH P4 | mAb6H8 (IgG₁ κ) | 250 | 41,000 | 106 |
| | (+)METH P6 | mAb6H4 (IgG₁ κ) | 11 | 4000 | 4 |
| | (+)METH PO6 | mAb6H7 (IgG₂ₐ κ) | 95 | 47,000 | 87 |
| | (+)METH MO6 | mAb9B11 (IgG₁ λ) | 41 | 5000 | 123 |
| | (+)METH MO10 | mAb4G9 (IgG₂ₐ κ) | 34 | 120 (51 nM with [³H]-(+) AMP) | 140 |

Example 2

MAb Cross Reactivity Studies

After screening over 25,000 potential hybridoma cell lines for mAb production, five mAb with the most favorable immu- Results RIA was used to determine the relative affinity and cross-reactivity profile of each mAb (Tables 1 and 2). Only one of five haptens generated mAb with the desired therapeutic potential. Immunization with the MO10 hapten resulted in production of mAb (mAb4G9) with high-affinity binding to (+)METH, (+)AMP, and (+)MDMA; little or no cross-reactivity with (−)METH-like isomers; and no significant cross-reactivity with endogenous compounds or structurally similar common medications (Tables 1 and 2).

TABLE 2

Characterization of the binding specificities of three important prototype anti-METH/MDMA or anti-METH/MDMA/AMP mAb.

| Drug | Antibody Specificity (IC$_{50}$ ratio as percent)[a] | | | |
|---|---|---|---|---|
| | mAb6H4 (11 nM)[b] | mAb6H8 (250 nM)[b] | mAb4G9 (34 nM)[b] | mAb2F11 |
| (+)METH | 100% | 100% | 100% | 100% |
| (+)AMP | 0.1% | 2.3% | 34% | 33% |
| (+)MDMA | 125% | 340% | 29% | 41% |
| (−)METH | 3% | 1.1% | 10.2% | 2.2% |
| (−)AMP | <0.1% | 0.3% | 6.3% | 5.3% |
| (−)MDMA | 0.7% | 1.8% | 1.1% | 0.6% |
| (+)MDA | 0.1% | 2.4% | 9.0% | nyd |
| (−)MDA | <0.1% | <0.1% | 0.2% | nyd |
| 4-OH-METH | 58.8% | 29.4% | 10.6% | nyd |
| (+)pseudoephedrine | <0.1% | 1.8% | 0.4% | nyd |
| (+)norpseudoephedrine | <0.1% | <0.1% | <0.1% | nyd |
| /-phenylphrine | 0.1% | <0.1% | <0.1% | nyd |
| (+)ephedrine | <0.1% | <0.1% | <0.1% | nyd |
| (+)phenylpropanolamine | <0.1% | <0.1% | <0.1% | nyd |
| β-phenylethylamine | <0.1% | <0.1% | 0.1% | nyd |
| tyramine | <0.1% | <0.1% | <0.1% | nyd |
| dopamine | <0.1% | <0.1% | <0.1% | nyd |
| norepinepherine | <0.1% | <0.1% | <0.1% | nyd |
| serotonin | <0.1% | <0.1% | <0.1% | nyd |
| epinephrine | <0.1% | <0.1% | <0.1% | nyd |

[a]IC$_{50}$ ratio = (RIA IC$_{50}$ value for METH/RIA IC$_{50}$ value for test ligand). See Table 1 for the structures of the haptens used to generate these antibodies.
[b]IC$_{50}$ value for METH binding from Table 1.
nyd: value not yet determined Since mAb4G9 was the only of the chosen five mAb to significantly cross-react with (+)AMP (Tables 1 and 2), its affinity for (+)AMP was examined in more detail. For this, a RIA analysis was conducted using [$^3$H]-(+)AMP (in addition to a RIA with [$^3$H]-(+)METH) and AMP as the inhibitor. These data showed the actual affinity for AMP was 51 nM (Table 1), demonstrating that this mAb has virtually the same $K_D$ value for AMP and METH. [$^3$H]-(+)MDMA was not available for determining a more accurate $K_D$ value for (+)MDMA binding, but it seems likely that the true $K_D$ value would be significantly lower than the value indicated by MDMA inhibition of [$^3$H]-(+)METH binding in the RIA.

Attaching the linker of the hapten distal to the chiral center of the molecule yielded a refined specificity for (+)-isomers (Table 2). The relatively short length of spacer arms of haptens (+)METH P4 and (+)METH P6 (4- and 6-carbon linkers, respectively), coupled with attachments at the para-carbon of the (+)METH phenyl ring (Table 1), hindered the flexibility of haptens. This likely forced the immune system to recognize the presence of the methyl group on the nitrogen molecule of (+)METH and (+)MDMA and its absence in (+)AMP. Thus, mAb affinity was high for (+)METH and (+)MDMA, but low for (+)AMP. The hapten (+)METH PO6, like (+)METH P6, was designed with a linker attached to the para-carbon of the phenyl ring, but an oxygen was included to influence localized charge and solubility and mimic the presence of one of two oxygen atoms at the para and meta positions of the methylenedioxy group of (+)MDMA (Table 1). An oxygen attached to the phenyl ring structure was included in two other haptens, (+)METH MO6 and (+)METH MO10, but linkers were attached to the meta-carbon of the phenyl ring of (+)METH. This strategy was designed to present the oxygen of the (+)MDMA-like structure along the same spatial plane as the (+)METH molecule's chiral center. The longer (+)METH MO10 spacer was used to allow more flexibility in the hapten on the protein in hopes of discovering mAb with broader recognition of (+)METH-like structures. These combined strategies resulted in the best balance of affinity and specificity.

From these studies, it was learned that 1) linkers located distal to the chiral center of this very small molecule favor generation of stereospecific antibodies, 2) a longer flexible linker arm like (+)METH MO10 favors generation of antibodies with broader selectivity for (+)METH-like compounds, and 3) spacers ≧6 atoms produce higher affinity mAb. Importantly, discovery of mAb4G9 was not an isolated event, as other MO10-derived mAb with similar specificities for (+)METH and (+)AMP have since been discovered.

Example 3

Antibody Sequence Analysis

To gain a better molecular understanding of how the primary amino acid sequence affected mAb affinity for (+)METH, related and unrelated sequence features in each mAb variable region was analyzed. Three of the mAb were IgG1 subclass and two were IgG2 (Table 1). Except for anti-METH/MDMA mAb9B11 (λ light chain), all of the mAb possessed a κ light chain.

cDNA cloning and sequencing of mAb. For these studies, five prototype anti-METH mAb ranging in METH affinities from 11 to 250 nM were analyzed (Table 1). A single prototype mAb resulting from each of the haptens was chosen for detailed studies. The light chain (LC, singular and plural) cDNA of the mAb were cloned by RT-PCR using Superscript II reverse transcriptase (Invitrogen) with an exact reverse primer matching the C-terminus of the LC named MLEND1.Not (5'-GGG GCG GCC GCG CGT CTC AGG ACC TTT GTC TCT AAC-3') (SEQ ID NO:1). The LCs of mAb6H4, mAb6H8, and mAb6H7 were amplified in the forward direction with the degenerate primer ML2, and the LC of mAb4G9 was amplified in the 5' direction with the degenerate primer ML4 (Coloma et al., 1992). The LC of mAb9B11 was amplified in the forward direction with the primer sequence 5'-ATGGCCTGGA(T/C)TTCACT-TATACTCTCTCTCCTGGCTCTC-3' (SEQ ID NO:2). The resulting cDNA was blunt-ligated into the Sma I site of the cloning vector pGEM-3Z.

The heavy chain cDNA of all IgG1 (from (+)METH P4, (+)METH P6 and (+)METH MO6) mAb were amplified using RT-PCR as described above with an exact reverse primer to the C-terminus of the heavy chain, named MHEND.NotI 5' GGG GCG GCC GCA GGG CTC CAA GGA CAC TGG GAT CAT TT 3' (SEQ ID NO:3), and a mixture of three degenerate primers based on the MHALT primers from Coloma et al. (1992, J Immunol Methods 152: 89-104). The primers were modified from the originally published sequence only by the substitution of a Nhe I restriction site for the original restriction site. The IgG2 mAb (from (+)METH PO6 and (+)METH MO10) were amplified with the reverse primer 5-CTCCCGGTCTCCGGGTAAATGA-3' (SEQ ID NO:4).

The forward sequence of the heavy chain of mAb6H8 was amplified with primer MHALT1 (Coloma et al, 1992, J Immunol Methods 152:89-104). The forward primers for mAb6H4, mAb6H7, mAb9B11, and mAb4G9 were designed from the results of N-terminal sequencing of the mature proteins (see FIGS. 1A and B for protein sequences). The primer sequences used were: 5'-GAGTGCAGCTTCAGGAGT-CAGGACCTAGC-3' (SEQ ID NO:5) for mAb6H4, 5'-GAT-GTAAAACTTCAGGAGTCAGGACCTGGC-CTCGTGAAACCTTCTCAGTC-3' (SEQ ID NO:6) for mAb6H7, 5'-GAGGTGCAGCTTCCGGAGTCAGGAC-CTAGC-3' (SEQ ID NO:7) for mAb9B11, and 5'-GAGTAC-CAGCTCCAGCAGTCTGGGAC-3' (SEQ ID NO:8) for mAb4G9. The cDNA was then blunt-ligated into the Sma I site of cloning vector pGEM-3Z. The resulting plasmids of all mAb cloning were transformed into *E. coli* strain DH5α and sequenced at University of Arkansas for Medical Sciences DNA Core Sequencing Facility.

All sequences were submitted to the GenBank database. The GenBank-assigned accession numbers for the following antibodies are listed here in parentheses (light chain, heavy chain): mAb6H8 (DQ381551, DQ381550), mAb6H4 (DQ381543, DQ381542); mAb6H7 (EF392838, EF392837); mAb9B11(EF392840, EF392839) and mAb4G9 (EF392842, EF392841). The germ-line usage of the different mAb was determined by comparing the DNA sequences to those in the IMGT database using the web-based program V-QUEST tools (Internet address: imgt.cines.fr) and by visual examination of the sequences (Giudicelli et al., 2004, Nuc Acid Res 32:W435-440).

Results. Alignments of the amino acid sequences of the variable region of the mAb are presented in FIG. 2. An analysis of complementarity determining regions revealed a high degree of diversity in both composition and length. The first light chain CDRs (L1) varied in length from 10-14 residues, and with the exception of mAb4G9, possessed a large number of serine residues (FIG. 2B). The only conserved residue in L1 CDR, or any of the light chain CDRs, was the serine at position L26. The L2 CDRs were 7 residues in length except for mAb6H7, which possessed only 5 amino acids. The L3 CDRs were all 9; residues in length except mAb4G9 which had 10 residues. The CDRs of the heavy chains (FIG. 2A) exhibited similar lengths in the H1 and H2 CDRs, but little homology. The H1 CDR had a conserved threonine at position H30 and either a tryptophan or tyrosine at position H33. The H3 CDRs differed in length from 8-16 residues. Although not immediately apparent from the alignment, all H3 regions possessed two tyrosine residues spaced five residues apart, with the second tyrosine before the tryptophan at H103.

While comparisons of CDR sequences are important, differences in CDRs can be attributed to differences in germ-line sequences of particular V-region genes, and to somatic mutation within the CDRs of these V-region genes. To better understand the relative importance of the germ-line and somatic mutations, the sequenced genes were analyzed using the IMGT database (Giudicelli et al., 2004, Nuc Acid Res 32:W435-440). The analysis showed that each antibody was unique and not clonal. That is, rather than coming from one germ-line gene arrangement early in B cell development, they resulted from unique V(D)J recombination events. These unique germ-line gene rearrangements then underwent somatic DNA mutations, that were often silent, but some resulted in amino acid changes that differed from the original germ-line gene. Thus, no clear pattern of response was found.

This sequence analysis elucidated unique sequence differences in the antibody CDRs. A common feature was a conserved proline at position 95 or 95a of all L3 CDR regions, except for mAb9B11 (FIG. 2B), which had a serine residue. Because of their ability to form "hinges," proline residues often lend flexibility in main chain protein sequences. This proline/serine was immediately followed by either a hydrophobic amino acid (i.e. leucine or valine as in mAb6H4 and mAb9B11, respectively) or an aromatic residue. It is possible that these residues could be important for interaction with the phenyl ring of (+)METH-like compounds via hydrophobic or pi-pi interactions, and the preceding proline could lend flexibility to adapt to different conformations.

Example 4

Molecular Modeling and Docking

Based on the results of the primary sequence alignment, three mAb (mAb6H4, mAb6H8 and mAb4G9) were chosen for structural modeling. Each CDR was assigned and given a canonical classification (Al-Lazikani et al., 1997, J Mol Biol 273:927-948), except for the H3 CDRs, which do not possess canonical classes.

IqG variable region structural modeling and analysis. Molecular modeling of the three dimensional structure of the variable regions of three of the mAb was performed using the WAM antibody modeling algorithm (Whitelegg and Rees, 2000, Protein Eng 13:819-824). mAb6H4, mAb6H8, and mAb4G9 were chosen for more detailed analysis because they exhibited the full range of affinities for (+)METH and a broad range of ligand specificities for other important METH-like drugs. The primary amino acid sequences of the variable regions of the HC (heavy chain) and LC were first submitted to the WAM antibody modeling site for alignment. The program aligned the sequences against known sequences in the database and searched for canonical classes of complementarity determining regions (CDR). Based on these classifications, the program assigned a 3-dimensional structure to the framework regions and CDRs by fitting the main chain to that of the closest known structures.

Ligand docking. For docking simulation, the FlexX (Tripos) program was used. First, a deep pocket was identified at the interface of the CDRs from surface modeling and electrostatic calculations in Pymol (Delano Scientific, San Carlos, Calif.) and Sybyl (Tripos). To define this region as a putative active site, residues within an area 6 Å around F L94 (for mAb6H4) or Y L94 (for mAb4G9) were selected. The METH ligand was assigned formal charges by Sybyl and the molecule was allowed partial flexibility. The program was set to find the 30 best docking conformations and return these in a consensus scoring table.

Results. The three-dimensional models exhibited classical antibody β-sheet fold conformation (FIG. 3). In general, all models showed conformity with geometrical constraints throughout the structures. The analysis indicated that less than 2% of residues had main chain ψ and φ angles in outlier regions. All three models appeared to conform reasonably well to known protein structural features and constraints, and they presented an appropriate foundation to conduct base docking analysis.

All CDRs fell within canonical classes except L3 of mAb4G9 and the H3 CDRs, which do not have canonical classes. The H3 CDRs of all three antibodies were predicted to form a kinked or "hairpin," rather than extended conformation. Comparison of the models revealed conserved structural elements and some potentially important differences in the root mean square deviations (RMSD) of the CDR loop configurations (FIG. 3). The loop structure of mAb6H4 was arbitrarily chosen as a reference point to compare the differences from the other two antibodies, because it had the highest affinity for (+)METH. The L2 CDRs of all three antibodies occupied nearly the same spatial positions. The L3 regions of mAb6H4 and mAb6H8 were very similar, even though they differed in affinity for (+)METH by about 25-fold.

Based on the modeling results, docking simulation was performed with mAb6H4 and mAb4G9. According to the models (FIG. 4), a deep pocket was formed by the interaction of the H1, H2, L1 and L3 CDR loops for both antibodies, with a wider pocket formed in the binding region of mAb4G9 due to a shorter H3 CDR. A theoretical docking of (+)METH was created into these mAb pockets and identified residues within 8 angstroms of the ligand as possible sites for ligand-mAb interaction (FIG. 4). The results of this FlexX-based docking indicated that the METH molecule was generally oriented with the hydrophobic phenyl group toward the interior of the pocket. In mAb6H4 and mAb4G9, the charged nitrogen of METH was in close proximity to a histidine at position L32 and H35 respectively.

Based on the molecular modeling analyses, the interface between (+)METH and the mAb was relatively small, (the surface area of (+)METH is 174 Å$^2$) with small shifts in protein conformation producing large changes in binding. As can be seen in FIG. 3, the most striking deviations appeared in the H3 CDR region, with over 6 Å and 7 Å RMSD in mAb6H8 and mAb4G9, respectively. The diversity in the positions of the CDR suggests that each of these antibodies exhibited a binding paradigm to (+)METH-like drugs that was somewhat independent of loop configuration. The surface rendering of the models exposed a deep pocket at the CDR interface of mAb6H4. This pocket appeared to be approximately the size of (+)METH and would likely accommodate docking of the ligand. By contrast, the potential binding pocket of mAb4G9 was wider and shallower. It is hypothesized that the longer linker arm of (+)METH MO10 combined with the changed dihedral angle of an oxygen at the meta position of the phenyl ring contributed to the formation of a larger pocket. Analysis indicated that only five of the six CDR loops, might be directly involved in binding of (+)METH-like drugs, with L2 showing little contact. The (+)METH docking simulation with FlexX indicated that the potential binding pockets were dominated by aromatic residues with some capable of making hydrogen bonds (i.e., histidine and tyrosine).

Example 5

Anti-(+)METH mAb Alter (+)METH Pharmacokinetics in Rats

The ability of anti-(+)METH mAb6H4 (generated against (+)METH P6 hapten, see Table 1) to alter (+)METH brain concentrations was examined in two different models of (+)METH abuse (Byrnes-Blake et al., 2005, Eur J Pharmacol 521:86-94).

The overdose model was designed to mimic a drug abuser taking a high iv (+)METH dose and treated with (+)METH mAb in the emergency room. In this model, rats received 1 mg/kg (+)METH (iv) followed 30 min later by an anti-(+)METH mAb dose. The mAb pretreatment model was designed to mimic an abuser in drug treatment administered an anti-(+)METH mAb medication at the start of behavioral modification therapy who relapses to (+)METH use. In this model, rats were pretreated with anti-(+)METH mAb6H4 and received a 1 mg/kg iv (+)METH dose the following day. This dose (without mAb) produced about 2.5 hrs of locomotor effects. Rats (3/time point) were sacrificed at varied times after (+)METH administration to determine (+)METH brain concentrations. mAb6H4 decreased (+)METH brain concentrations in both models. Indeed, (+)METH brain concentrations in both models were virtually superimposable at comparable times after 30 min—the time of mAb administration in the overdose model. Both studies clearly show that antibodies against (+)METH can significantly reduce (+)METH brain concentrations over time.

Next, the "functional" half-life of each of the afore-mentioned anti-(+)METH mAb (see Table 1) was determined. This "functional" assay compared (+)METH concentrations in the absence and presence of mAb. By this measure, the best antibodies are those with the highest and longest increases in serum (+)METH and (+)AMP concentrations. First, it was determined that the pharmacokinetic properties of the mAb were not different (results not shown). For instance, they all had a serum half-life of about 7-8 days, which ruled out the possibility that one or more of them were quickly cleared and thus inactivated through elimination. It also showed the potential to produce a long-acting anti-(+)METH therapy by passive or active immunization.

Figure 5:
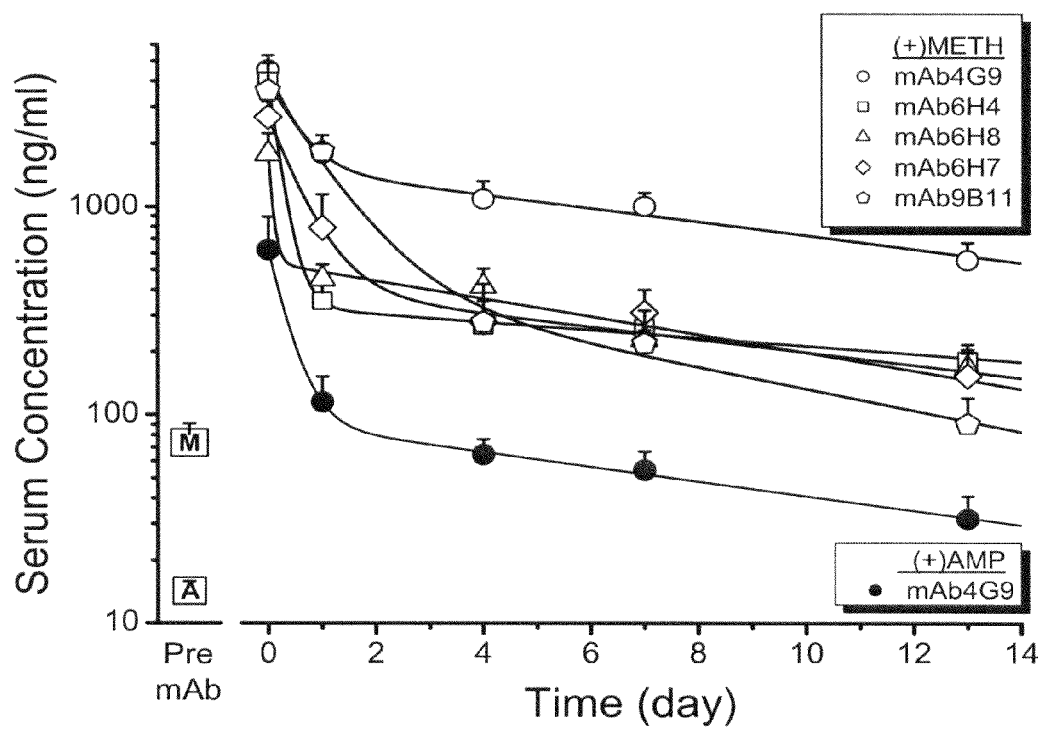
FIG. 5 presents a graph depicting serum concentration of (+)METH over time. (+)METH concentrations before (□ symbol with "M" inside) and after treatment (open symbols) with five different anti-(+)METH mAb (n=3 rats/time point) and (+)AMP concentrations before (□ symbol with "A" inside) and after treatment (filled circles) with mAb4G9. (+)AMP concentrations (filled circles) are shown only for mAb4G9 because the other four mAb did not produce long-term increases in (+)AMP concentrations. The best-fit line was determined using a weighted two-compartment pharmacokinetic model.

To conduct the "functional" studies, male rats (n=4/group) were given 14-day continuous (+)METH infusions at 5.6 mg/kg/day by sc osmotic minipumps. After achieving steady state (+)METH concentrations (at 24 hrs), each rat was treated with a dose of mAb that was equimolar in binding sites to the steady-state body burden of (+)METH. Only a single dose of mAb was administered at this time point, but (+)METH was continuously infused at a rate of 50% of the body burden per hour to maintain a (+)METH steady state. Serum samples were collected pre-mAb and at time points after mAb administration. All anti-(+)METH mAb caused significant acute increases in serum (+)METH concentrations compared with pre-mAb controls. However, there were substantial differences in serum (+)METH concentration vs. time curves for the five mAb (FIG. 5, open symbols). Most anti-(+)METH mAb appeared to be partially inactivated to differing degrees over time, as judged by their inability to maintain high concentrations of (+)METH in serum over time. This inactivation was particularly striking for the highest affinity mAb6H4 ($K_D$=11 nM). However, mAb4G9 ((+)METH and (+)AMP, $K_D$=34 and 51 nM, respectively) was still very effective after about 2 wks. It was also the only mAb that maintained significantly increased concentrations of (+)AMP (closed circles) and (+)METH (open circles) over time compared to pre-mAb concentrations (square symbols with "A" and "M" inside).

It was originally hypothesized that mAb affinity was the primary driving force for therapeutic efficacy. However, these studies revealed that the duration of action and function of the anti-(+)METH mAb in vivo was decreased, while the mAb protein pharmacokinetics were not different (similar $t_{1/2}$, clearance, and volume of distribution values). This was unanticipated. The first generation of haptens (e.g., (+)METH P6 and (+)METH P4) were purposely designed to produce mAb specific for (+)METH, with virtually no cross reactivity with (+)AMP. When the second generation of haptens (e.g., (+)METH MO10) were produced, it was discovered that the resulting mAb, with specificity for (+)METH and (+)AMP, had the clinically important advantages of increased duration of action and efficacy.

For instance (see FIGS. 7 and 8) mAb4G9 substantially alters the disposition of AMP, unlike mAb6H4 (generated by the P6 hapten). As shown in FIG. 8, mAb4G9 reduces both METH and AMP concentrations in the brain, which is medically important. It also repartitions AMP into the serum from other compartments (FIG. 7). mAb6H4 has minimal or no effect on AMP in either brain or serum because it is not broadly specific in vivo.

Furthermore, mAb4G9 has a longer functional half-life than mAb generated by previous haptens. FIG. 7 shows mAb6H4 has significantly less in vivo functionality (increased serum levels of METH/AMP is an indication of activity) by the 24 h timepoint. In contrast, mAb4G9 maintains significantly elevated serum METH and AMP concentrations 24 h after administration, indicating extended in vivo functionality.

Example 6

Behavioral Assays

Figure 6:
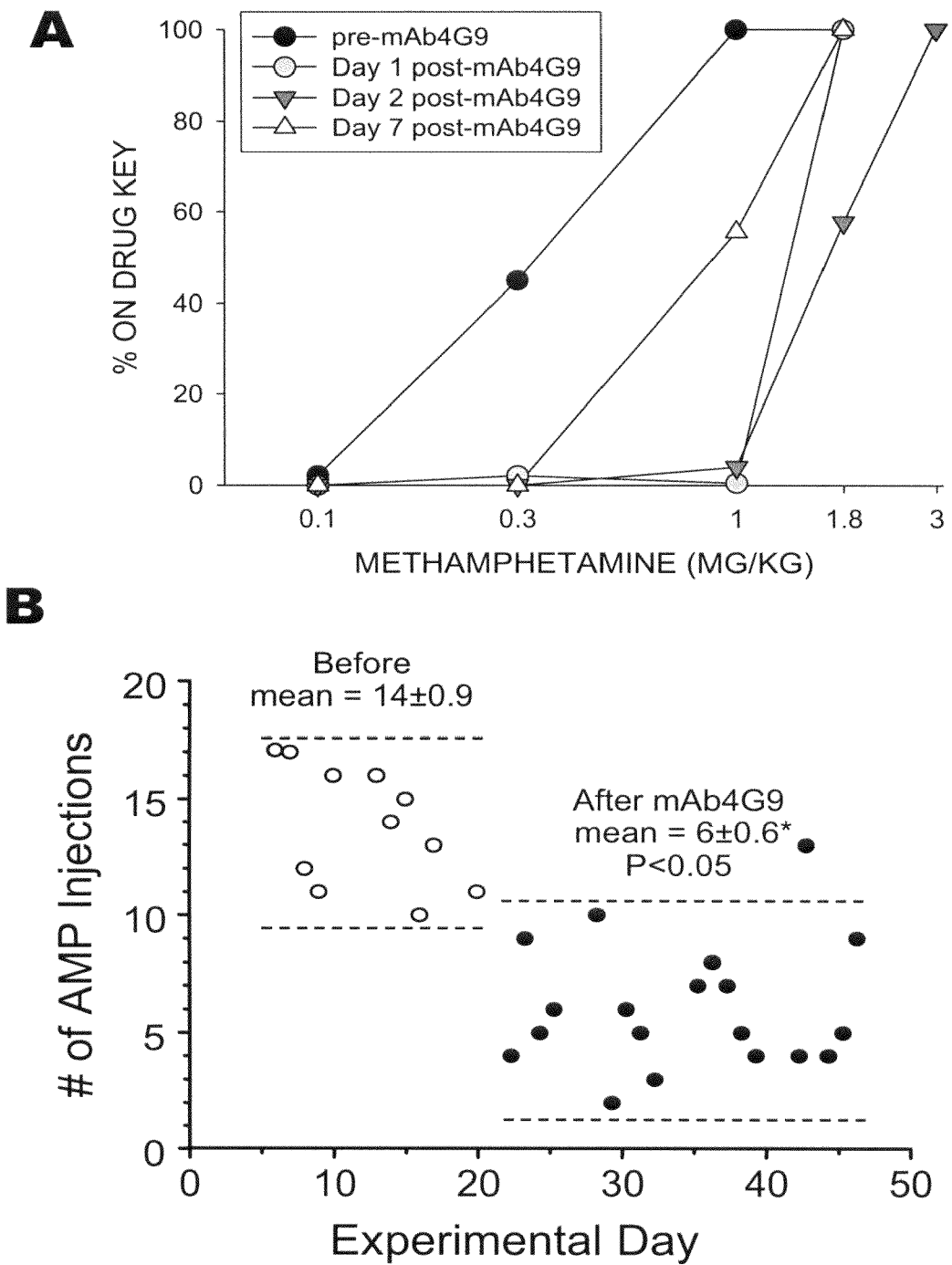
FIG. 6 presents graphs depicting the effect of mAb4G9 on METH discrimination (Panel A) and AMP self-administration (Panel B) in rats. (A) Rats were trained to discriminate cocaine and METH and then administered mAb4G9. Drug discrimination dose response curves were then determined for METH. (B) (+)AMP self-administration before and after treatment with mAb4G9 (3-4 rats/time point). Dashed lines are used to show the groupings of responding for (+)AMP before and after mAb. *$P<0.05$ compared to control group before antibody (open circles).

The in vivo effects of mAb4G9 were examined using a drug discrimination model. mAb4G9 appeared to be an effective and long-lasting antagonist of METH effects in this model (FIG. 6A). The mAb4G9 (600 mg/kg) shifted the dose response curves for at least 7 days. On the first and second day after mAb treatment, the dose response curve was shifted about 4- to 6-fold. When tested again at 7 days after mAb4G9 treatment, the dose response curve was still shifted about 2.5 fold.

We also tested the ability of mAb4G9 to block (+)AMP self-administration in a model in which rats responded under a fixed interval (60 sec) paradigm for a dose of 0.03 mg/kg (+)AMP per infusion. As shown in FIG. 6B, the number of (+)AMP injections per session was significantly reduced after mAb4G9 administration (100 mg/kg). Thus, mAb4G9 dramatically reduced responding for (+)AMP. These studies suggest that a single mAb could help prevent relapse to (+)METH and/or (+)AMP use.

What is claimed is:

1. An isolated monoclonal antibody that recognizes each compound of the group consisting of (+)amphetamine, (+)methamphetamine, and (+)3,4-methylenedioxymethamphetamine, and does not substantially recognize each compound of the group consisting of (−)amphetamine, (−)methamphetamine, and (−)3,4-methylenedioxymethamphetamine, wherein the antibody is generated using a immunizing agent comprising the formula

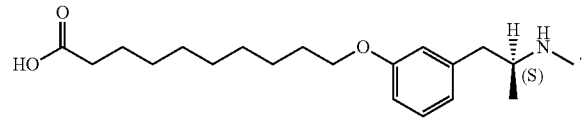

2. The isolated monoclonal antibody of claim 1, wherein the antibody has an $IC_{50}$ ratio calculated in reference to (+)methamphetamine of less than about 12% for each compound of the group consisting of (−)amphetamine, (−) methamphetamine, and (−)3,4-methylenedioxymethamphetamine.

3. The isolated monoclonal antibody of claim 1, wherein the antibody has an $IC_{50}$ ratio calculated in reference to (+)methamphetamine of greater than about 25% for each compound of the group consisting of (+)amphetamine, (+)methamphetamine, and (+)3,4-methylenedioxymethamphetamine.

4. The isolated monoclonal antibody of claim 3, wherein the antibody has an $IC_{50}$ ratio calculated in reference to (+)methamphetamine of less than about 12% for each compound of the group consisting of (−)amphetamine, (−) methamphetamine, and (−)3,4-methylenedioxymethamphetamine.

5. The isolated monoclonal antibody of claim 1, wherein the heavy chain of the antibody comprises the amino acid sequence of SEQ ID NO:25, and the light chain of the antibody comprises the amino acid sequence of SEQ ID NO:26.

6. The isolated monoclonal antibody of claim 1, wherein the heavy chain of the antibody comprises the amino acid sequence of SEQ ID NO:19, and the light chain of the antibody comprises the amino acid sequence of SEQ ID NO:21.

7. The isolated monoclonal antibody of claim 1, wherein the antibody is selected from the group consisting of a murine antibody, a human antibody, a humanized antibody, a chimeric antibody, a recombinant antibody, and an antigen binding fragment of an antibody.

8. A method of treating drug use in a subject, the method comprising administering a monoclonal antibody of claim 1 to the subject, wherein the monoclonal antibody decreases the concentration of (+)amphetamine, (+)methamphetamine, and (+)3,4-methylenedioxymethamphetamine in the brain of the subject.

9. The method of claim 8, wherein the subject is selected from the group comprising a rodent, a non-human primate, and a human.

10. A method of treating drug use in a subject, the method comprising administering a monoclonal antibody of claim 1 to the subject, wherein the monoclonal antibody decreases the concentration of (+)amphetamine, (+)methamphetamine, or (+)3,4-methylenedioxymethamphetamine in the brain of the subject.

11. The method of claim 10, wherein the subject is selected from the group comprising a rodent, a non-human primate, and a human.

12. A method for detecting the presence of at least one compound in a sample selected from the group of compounds consisting of (+)methamphetamine, (+)amphetamine, and (+)3,4-methylenedioxymethamphetamine, the assay comprising contacting the sample with a monoclonal antibody of claim 1 and detecting the association of the monoclonal antibody in the sample with at least one compound selected from the group consisting of (+)methamphetamine, (+)amphetamine, and (+)3,4-methylenedioxymethamphetamine.

13. The method of claim 12, wherein the sample is a biological sample or a chemical sample.

14. The method of claim 13, wherein the biological sample is a biological fluid.

15. The method of claim 12, wherein the association is detected by a means selected from the group consisting of ELISA, immunochromatographic assay, and immunoprecipitation assay.

16. The method of claim 12, wherein the assay further comprises quantifying the amount of a compound selected from the group of compounds consisting of (+)methamphetamine, (+)amphetamine, and (+)3,4-methylenedioxymethamphetamine in the sample.

17. A kit, wherein the kit comprises a monoclonal antibody that recognizes each compound of the group consisting of (+)amphetamine, (+)methamphetamine, and (+)3,4-methylenedioxymethamphetamine, and does not substantially recognize each compound of the group consisting of (−)amphetamine, (−) methamphetamine, and (−)3,4-methylenedioxymethamphetamine, wherein the antibody is generated using a immunizing agent comprising the formula

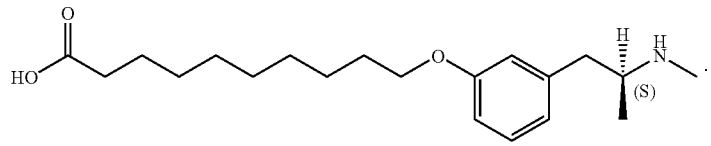

\* \* \* \* \*

UNITED STATES PATENT AND TRADEMARK OFFICE
CERTIFICATE OF CORRECTION

PATENT NO.        : 7,858,756 B2
APPLICATION NO.   : 11/763948
DATED             : December 28, 2010
INVENTOR(S)       : S. Michael Owens et al.

It is certified that error appears in the above-identified patent and that said Letters Patent is hereby corrected as shown below:

Column 1, lines 16-18, cancel the sentence beginning with "This invention was" and ending with "Drug Abuse." and insert the following sentence:

--This invention was made with government support under DA011560, DA014361 and DA005477 awarded by the National Institutes of Health.--

Signed and Sealed this
Seventeenth Day of April, 2012

David J. Kappos
*Director of the United States Patent and Trademark Office*